United States Patent
Mohrman et al.

(10) Patent No.: US 12,059,267 B2
(45) Date of Patent: Aug. 13, 2024

(54) EXPENDITURE TO OVERCOME AIR RESISTANCE DURING BIPEDAL MOTION

(71) Applicant: STRYD, INC., Boulder, CO (US)

(72) Inventors: Wyatt Mohrman, Boulder, CO (US); James Williamson, Broomfield, CO (US); Kristine Snyder, Boulder, CO (US); Kun Li, Broomfield, CO (US); Li Shang, Boulder, CO (US); Robert P. Dick, Chelsea, MI (US)

(73) Assignee: STRYD, INC., Boulder, CO (US)

( * ) Notice: Subject to any disclaimer, the term of this patent is extended or adjusted under 35 U.S.C. 154(b) by 487 days.

(21) Appl. No.: 16/914,253

(22) Filed: Jun. 26, 2020

(65) Prior Publication Data

US 2020/0405231 A1 Dec. 31, 2020

Related U.S. Application Data

(60) Provisional application No. 62/867,201, filed on Jun. 26, 2019.

(51) Int. Cl.
*A61B 5/00* (2006.01)
*A61B 5/11* (2006.01)

(52) U.S. Cl.
CPC ............ *A61B 5/4866* (2013.01); *A61B 5/112* (2013.01); *A61B 5/7246* (2013.01);
(Continued)

(58) Field of Classification Search
None
See application file for complete search history.

(56) References Cited

U.S. PATENT DOCUMENTS

| 5,043,692 A | 8/1991 | Sites et al. |
| 5,125,412 A | 6/1992 | Thornton |

(Continued)

FOREIGN PATENT DOCUMENTS

| CN | 202876289 U | 4/2013 |
| DE | 102018213035 A1 | 2/2020 |

(Continued)

OTHER PUBLICATIONS

Anastasopoulou, P. et al., "Using Support Vector Regression for Assessing Human Energy Expenditure Using a Triaxial Accelerometer and a Barometer," In: Godara B., Nikita K.S. (eds) Wireless Mobile Communication and Healthcare. MobilHealth 2012. Lecture Notes of the Institute for Computer Sciences, Social Informatics and Telecommunications Engineering, vol. 61. Springer, Berlin, Heidelberg; https://doi.org/10.1007/978-3-642-37893-5_12, 8 pages.

(Continued)

*Primary Examiner* — Benjamin S Melhus
(74) *Attorney, Agent, or Firm* — COOLEY LLP

(57) ABSTRACT

Systems and methods for determining the impact of air resistance on the power being produced by a body motion are disclosed. In one aspect, a method includes measuring positions and orientations of a portion of the body in motion. The method further includes measuring pressure experienced by the portion of the body in motion. The motion further includes calculating a static pressure based on the measured pressures and correlated position and orientation measurements. The method further includes calculating a maximum pressure and calculating an air induced power exerted on the body in motion.

27 Claims, 15 Drawing Sheets

(52) U.S. Cl.
CPC ........ *A61B 5/7278* (2013.01); *A61B 2503/40* (2013.01); *A61B 2560/0252* (2013.01); *A61B 2560/0257* (2013.01); *A61B 2562/0219* (2013.01); *A61B 2562/029* (2013.01)

(56) References Cited

U.S. PATENT DOCUMENTS

| | | |
|---|---|---|
| 5,899,963 A | 5/1999 | Hutchings |
| 6,052,654 A | 4/2000 | Gaudet et al. |
| 6,175,608 B1 | 1/2001 | Pyles et al. |
| 6,464,485 B1 | 10/2002 | Iida et al. |
| 6,493,652 B1 | 12/2002 | Ohlenbusch et al. |
| 6,496,779 B1 | 12/2002 | Hwang |
| 7,237,446 B2 | 7/2007 | Chan et al. |
| 7,383,728 B2 | 6/2008 | Noble et al. |
| D598,113 S | 8/2009 | Flaction et al. |
| 7,634,379 B2 | 12/2009 | Noble |
| 7,643,873 B2 | 1/2010 | Chan |
| 7,753,861 B1 | 7/2010 | Kahn et al. |
| 8,060,337 B2 | 11/2011 | Kulach et al. |
| 8,157,707 B2 | 4/2012 | Flaction |
| 8,655,618 B2 | 2/2014 | Flaction et al. |
| 8,718,938 B2 | 5/2014 | Wolf et al. |
| 8,840,569 B2 | 9/2014 | Flaction et al. |
| 9,433,843 B2 | 9/2016 | Morlock |
| 9,888,868 B2 | 2/2018 | Sarrafzadeh et al. |
| 10,744,371 B2 | 8/2020 | Mohrman et al. |
| 11,278,765 B2 | 3/2022 | Mohrman et al. |
| 2005/0075586 A1 | 4/2005 | Jamsen |
| 2006/0136173 A1* | 6/2006 | Case, Jr. ............. G01C 22/006 702/182 |
| 2007/0068273 A1 | 3/2007 | Cunningham |
| 2007/0260418 A1 | 11/2007 | Ladetto et al. |
| 2007/0287596 A1* | 12/2007 | Case, Jr. ............ A63B 24/0021 482/8 |
| 2008/0288200 A1 | 11/2008 | Noble |
| 2010/0211349 A1 | 8/2010 | Flaction et al. |
| 2010/0292941 A1 | 11/2010 | Grasso |
| 2010/0317489 A1 | 12/2010 | Flaction |
| 2011/0022349 A1 | 1/2011 | Stirling et al. |
| 2011/0207581 A1 | 8/2011 | Flaction |
| 2011/0231101 A1 | 9/2011 | Bidargaddi et al. |
| 2011/0313705 A1 | 12/2011 | Esser et al. |
| 2012/0130673 A1 | 5/2012 | Dishongh et al. |
| 2012/0232430 A1 | 9/2012 | Boissy et al. |
| 2013/0041617 A1 | 2/2013 | Pease et al. |
| 2013/0053990 A1 | 2/2013 | Ackland |
| 2013/0178958 A1 | 7/2013 | Kulach et al. |
| 2013/0190657 A1 | 7/2013 | Flaction et al. |
| 2013/0190658 A1 | 7/2013 | Flaction et al. |
| 2013/0338802 A1 | 12/2013 | Winsper et al. |
| 2014/0277633 A1 | 9/2014 | Flaction |
| 2014/0350703 A1 | 11/2014 | Flaction |
| 2015/0025817 A1 | 1/2015 | Ten Kate |
| 2017/0074897 A1* | 3/2017 | Mermel ................. A63B 69/16 |
| 2017/0189752 A1* | 7/2017 | Mohrman ............ A63B 24/0006 |
| 2021/0000386 A1* | 1/2021 | Whiteman ............ G16H 20/30 |

FOREIGN PATENT DOCUMENTS

| | | |
|---|---|---|
| EP | 2654030 A1 | 10/2013 |
| WO | WO-2007008930 A2 | 1/2007 |
| WO | WO-2007107491 A1 | 9/2007 |
| WO | WO-2008143738 A1 | 11/2008 |
| WO | WO-2009024600 A1 | 2/2009 |
| WO | WO-2010046448 A1 | 4/2010 |
| WO | WO-2012071551 A1 | 5/2012 |
| WO | WO-2015075307 A1 | 5/2015 |
| WO | WO-2017197524 A1 | 11/2017 |

OTHER PUBLICATIONS

Bouten, C. V. et al., "Assessment of energy expenditure for physical activity using a triaxial accelerometer," Official Journal of the American College of Sports Medicine, pp. 1519-1523 (1994).

Brodie, M. et al., "Fusion motion capture: a prototype system using inertial measurement units and GPS for the biomechanical analysis of ski racing," Sports Technol., 1(1):17-28 (2008).

Chen, D. et al., "A Wireless Real-time Fall Detecting System Based on Barometer and Accelerometer," 2012 7th IEEE Conference on Industrial Electronics and Applications (ICIEA), 2012, 6 pages.

Cooper, D. M. et al., "Aerobic parameters of exercise as a function of body size during growth in children," Journal of Applied Physiology, 56(3):628-634 (1984).

Estimate. (1992). In C. G. Morris (Ed.), Academic Press Dictionary of Science and Technology (4th ed.). Oxford, UK: Elsevier Science & Technology. Retrieved from https://search.credoreference.com/content/entry/apdst/estimate/0?institutionId=743, 2 pages.

Estimate. (2016). In Editors of the American Heritage Dictionaries (Ed.), The American Heritage Dictionary of the English Language (6th ed.). Boston, MA; Houghton Mifflin. Retrieved from: https://search.credoreference.com/content/entry/hm,dictenglang/estimate/0?instituionId=743, 2 pages.

Extended European Search Report dated Aug. 31, 2018 for European Application No. 15841179.3, 16 pages.

Extended European Search Report for European Application No. EP20830653 dated Jun. 15, 2023, 8 pages.

Final Office Action mailed Apr. 8, 2021 for U.S. Appl. No. 15/463,261, 9 pages.

Final Office Action mailed Jun. 20, 2018 for U.S. Appl. No. 15/794,762, 18 pages.

International Search Report and Written Opinion mailed Jan. 28, 2016 for International Application No. PCT/US15/51181, 14 pages.

International Search Report and Written Opinion mailed Oct. 29, 2020 for International Application No. PCT/US2020/40012, 11 pages.

Internet Archive. Xsens Website, "IMU Inertial Measurement Unit; Xsens 3D motion tracking," Mar. 21, 2014. Retrieved from https://web.archive.org/web/20140321235531/http://www.xsens.com/tags/imu/, 3 pages.

Lindsey, J. Outside Online. "The Science Behind Styrd, the World's First Running Power Meter," May 27, 2015. Retrieved from https://www.outsideonline.com/1981811/science-behind-stryd-worlds-first-running-power-meter, 8 pages.

Margaria, R. et al., "Energy cost of running," Journal of Applied Physiology, 18(2):367-370 (1963).

Non-Final Office Action mailed Dec. 28, 2017 for U.S. Appl. No. 15/794,762, 16 pages.

Non-Final Office Action mailed Oct. 10, 2019 for U.S. Appl. No. 15/794,762, 10 pages.

Non-Final Office Action mailed Sep. 18, 2019 for U.S. Appl. No. 15/463,261, 15 pages.

Non-Final Office Action mailed Jun. 18, 2020 for U.S. Appl. No. 15/463,261, 15 pages.

Ohtaki, Y. et al., "Automatic classification of ambulatory movements and evaluation of energy consumptions utilizing accelerometers and a barometer," Microsyst Technol, 11:1034-1040 (2005).

Omron Healthcare Inc., Omron Instruction Manual, Pocket Pedometer, 2010, 28 pages.

Partial Supplementary European Search Report dated May 3, 2018 for European Application No. 15841179.3, 14 pages.

Umberger, B. R. et al., "A model of human muscle energy expenditure," Computer Methods in Biomechanics and Biomedical Engineering, 6(2):99-111 (2003).

\* cited by examiner

500
EXPENDITURE TO OVERCOME AIR RESISTANCE DURING BIPEDAL MOTION

CROSS-REFERENCE TO RELATED PATENT APPLICATIONS

This application claims priority to U.S. Provisional Application No. 62/867,201, titled "EXPENDITURE TO OVERCOME AIR RESISTANCE DURING BIPEDAL MOTION," filed Jun. 26, 2019, which is hereby incorporated herein by reference in its entirety.

TECHNOLOGICAL FIELD

Embodiments described herein generally relate to determining the impact of air resistance on the power being produced by a human body during bipedal motion.

BACKGROUND

Inertial measurement units may be used to estimate the motion and positions of people engaging in bipedal motion, and the motion, positions, and orientations of portions of their bodies. Various methods may calculate the power exerted on moving objects given information about elapsed time, velocity, and force. Measurement devices may combine computer processors, memory, wireless transceivers, and sensors into wearable sensing systems. Various methods may track the motion of the human body in order to determine the power being applied to itself by its muscles. For example, international patent application no. PCT/US2015/051181, filed Sep. 21, 2015, which is hereby incorporated by reference in its entirety, includes disclosure of some such methods and provides background material useful in understanding the present disclosure. What is needed is a method of determining the power being applied to a human body by its own muscles in the presence of air resistance and/or in the presence of moving air or wind.

SUMMARY

It is an object of some embodiments described in this application to determine the power being exerted by a human body's muscles on that body in the presence of air resistance and/or wind, using dynamically changing data gathered using a compact body-mounted wireless sensing system containing one or more of the following sensor types: three-axis accelerometers, gyroscopes, magnetometers, (Global Positioning System) GPS receivers, barometric pressure sensors, ambient air temperature sensors, and relative humidity sensors. Various components within the sensing system may be connected using wires or wireless communication technologies. They may be physically connected or distributed among several locations on or near the body. It is also an object of this invention to display and record the power determined as described above. This power measurement may be used to assist athletic training.

Air, whether stationary or moving (i.e., wind), impart a drag force on a body and influence the power required to walk or run through the air mass. Depending on air mass movement relative to human body movement, the imparted drag force due to the air mass can increase or reduce energy production requirements needed to maintain a particular body speed and heading. Embodiments of a sensing system described herein incorporate implementations of signal processing techniques to determine the impact of air resistance on the body power consumption required to walk and run via motion sensing and ambient air sensing.

Some embodiments described herein relate to a device that may include a first pressure sensor configured to measure an anterior air pressure anterior to an animal body in motion. The device may further include a second pressure sensor configured to measure a posterior air pressure posterior to the animal body in motion. The device may further include a hygrometer configured to measure a humidity level. The device may further include a temperature sensor configured to measure a temperature. The device may further include a processor configured to calculate an air resistance experienced by the animal body based on the humidity level, the temperature, and a difference between the anterior air pressure and the posterior air pressure.

some embodiments described herein relate to a method that includes measuring, using a sensor module that includes an inertial measurement unit (IMU), multiple positions and orientation measurements of a portion of an animal body in motion. The method may further include measuring, using a pressure sensor of the sensor module, multiple measured pressures experienced by the portion of the animal body. The method may further include correlating each measured pressure from the plurality of measured pressures to a position and orientation measurement from the plurality of position and orientation measurements. The method may further include calculating, by a processor, a static pressure based on the measured pressures and the correlated position and orientation measurements. The method may further include calculating, by the processor, a maximum pressure of the measured pressures. The method may further include calculating an air-induced power exerted on the animal body based on the static pressure and the maximum pressure.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION

Figure 1A:
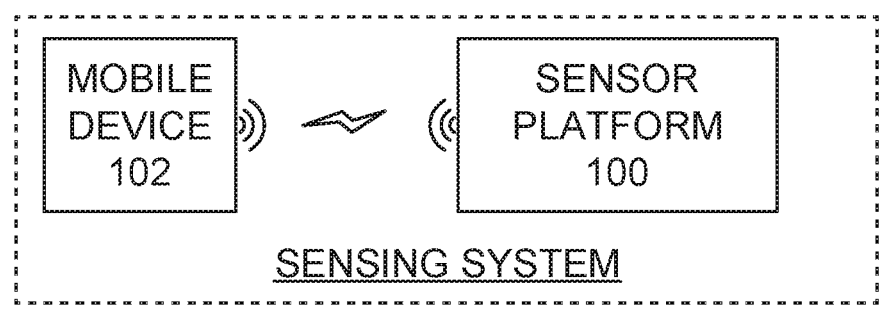
FIG. 1A shows a sensing system for sensing motion of a user during an activity, according to some embodiments.

Wearable sensor platforms and sensing systems described herein can sense motion and estimate power (i.e., mechanical power or biomechanical power) that a human body expends during physical activities such as running and other forms of bipedal motion. Training at the proper level of effort may be important for athletes whose objective is to achieve the best results in the least time. In running, for example, pacing (i.e., maintaining a desired speed) can be a useful metric to target, e.g., to improve endurance. However, pace alone is often not sufficient for achieving optimal or consistent results. For example, maintaining a runner's pace in the presence of wind, or on hilly terrain, can lead to early fatigue and/or reduced performance. Furthermore, measuring pace alone does not reveal specific issues regarding running form, efficiency, or technique, much less inform how training should be modified to improve performance or fitness.

Embodiments of an inventive sensing system and wearable sensor platform described herein, however, sense environmental and kinematic measures to quantify the effect of wind, sense motion, and provide real-time feedback to a user/wearer of their power expenditure during an activity. By actively monitoring their power expenditure, including power expenditure due to wind, an athlete can readily observe how changes in their technique (e.g., stride, body positioning, pace, cadence, etc.) impact their efficiency in different environmental conditions, and make adjustments to their technique accordingly, for example to minimize the power that he is expending when facing a headwind. As such, through use of the sensor platform, the user will naturally modify their technique in ways that result in more efficient running forms, and that reduce the "wear and tear" experienced by their body during the activity. Also, using the example of the running scenario noted above, by targeting or maintaining a desired power expenditure (instead of a pace) on hilly terrain, the user can achieve faster overall times on a course by redistributing their effort and avoiding premature fatigue. Furthermore, by monitoring their capacity to produce and sustain power, an athlete can better assess their fitness level, as well as monitor how their training is affecting their fitness level over time.

Embedded hardware/software sensing systems of the present disclosure use a variety of signal processing techniques to calculate wind velocity, forces due to air resistance, power expenditure to overcome air resistances, and activity-specific metrics of merit for those involved in bipedal activities, such as walking, running, dancing, and/or the like. To provide a user with customized, automated and/or manual advice on physical activity, time-dependent distributions of physiological and/or motion-related metrics for a user are measured/sensed by the sensor platform and used to inform automated and manual advice that is provided to the user via the sensing system. Applications of the present disclosure include reducing injury risk, improving athletic performance, improving the benefits of training sessions, enabling physical collaboration, and enabling motion-based control over other devices.

Functionalities of the disclosed system can include: (1) measuring environmental, physiological, and motion-related data with one or more sensors (e.g., within a sensor platform), each of which may have one or more sensors as well as wired or wireless communication interfaces; (2) computing metrics of interest based on these data, either on the same module that gathered the data or after wired or wireless transmission to another module; and/or (3) displaying metrics of interest (e.g., via a user interface) to users of the system and providing advice on how to change their activity, form, or technique to achieve better training, competition, and/or recovery results. These functionalities may be distributed across different physical modules, some of which may be computing/communication devices from third parties, such as smart phones, smart watches, and/or other computing devices. They may also be integrated into one or more physical modules. For example, any of the functionalities described herein may be performed within the sensor platform, within a mobile device that is separate from the sensor platform (e.g., a smart phone in wireless communication with the sensor platform) or shared between the sensor platform and the mobile device.

The described sensing system may have one or more of the following capabilities: 1) measure real-time barometric pressure sensed from anterior and/or posterior facing, and/or side facing, surface and/or surfaces of the body of a runner, 2) measure the ambient temperature of the air mass surrounding a runner, 3) measure the ambient relative humidity of the air mass surrounding a runner, 4) determine the current global position of a runner, 5) determine the real-time instantaneous velocity of a runner, 6) determine the real-time instantaneous position, velocity, and orientation of the sensor attachment point on the body of a runner, (e.g., a foot), 7) identify when the gait phase of individual in bipedal motion, including the swing phase, stance phase, and/or double stance phase, 8) calculate the air density of the air mass surrounding a runner, as a function of temperature, relative humidity, and/or elevation, 8) calculate a static pressure, a dynamic pressure, and/or a total pressure based on sensed data, 9) calculate a velocity.

Wearable Sensor Platform—Physical Description

Sensing devices (or "sensor platforms") of the present disclosure can include multiple sensors, such as inertial measurement units (IMUs, which can include accelerometers (e.g., one-axis, two-axis or three-axis accelerometers), gyroscopes, and/or magnetometers), temperature sensors, hygrometers, inertial sensors, force sensors, pressure sensors, Global Positioning System (GPS) receivers, and flex sensors, as well as local digital and analog signal processing hardware, storage device(s), energy source(s), and wireless transceivers integrated into apparel and/or wearable accessories relevant to bipedal motion, such as shoes, insoles, socks, leg bands, arm bands, chest straps, wrist bands/bracelets, and/or the like. Some of the aforementioned sensors, such as accelerometers, gyroscopes and magnetometers, can function as orientation sensors. The sensor platform may contain or be attached/operably coupled to more than one sensor of each type. Additional interface devices and computation devices capable of communicating with the sensor platform may also be used.

FIG. 1A shows an exemplary sensing system for sensing motion of a user, in which a sensor platform 100 is configured to wirelessly communicate with a mobile device 102 (e.g., a smart phone) and/or a communications network via a wireless communications link (e.g., using one or more RF protocols such as Bluetooth LE, Bluetooth, Wi-Fi, and/or Zigbee). In some embodiments, the sensor platform is also configured for wired communication (e.g., via an Ethernet cable, universal serial bus (USB), etc.) with the mobile device 102, personal computer, tablet, and/or the like.

Figure 1B:
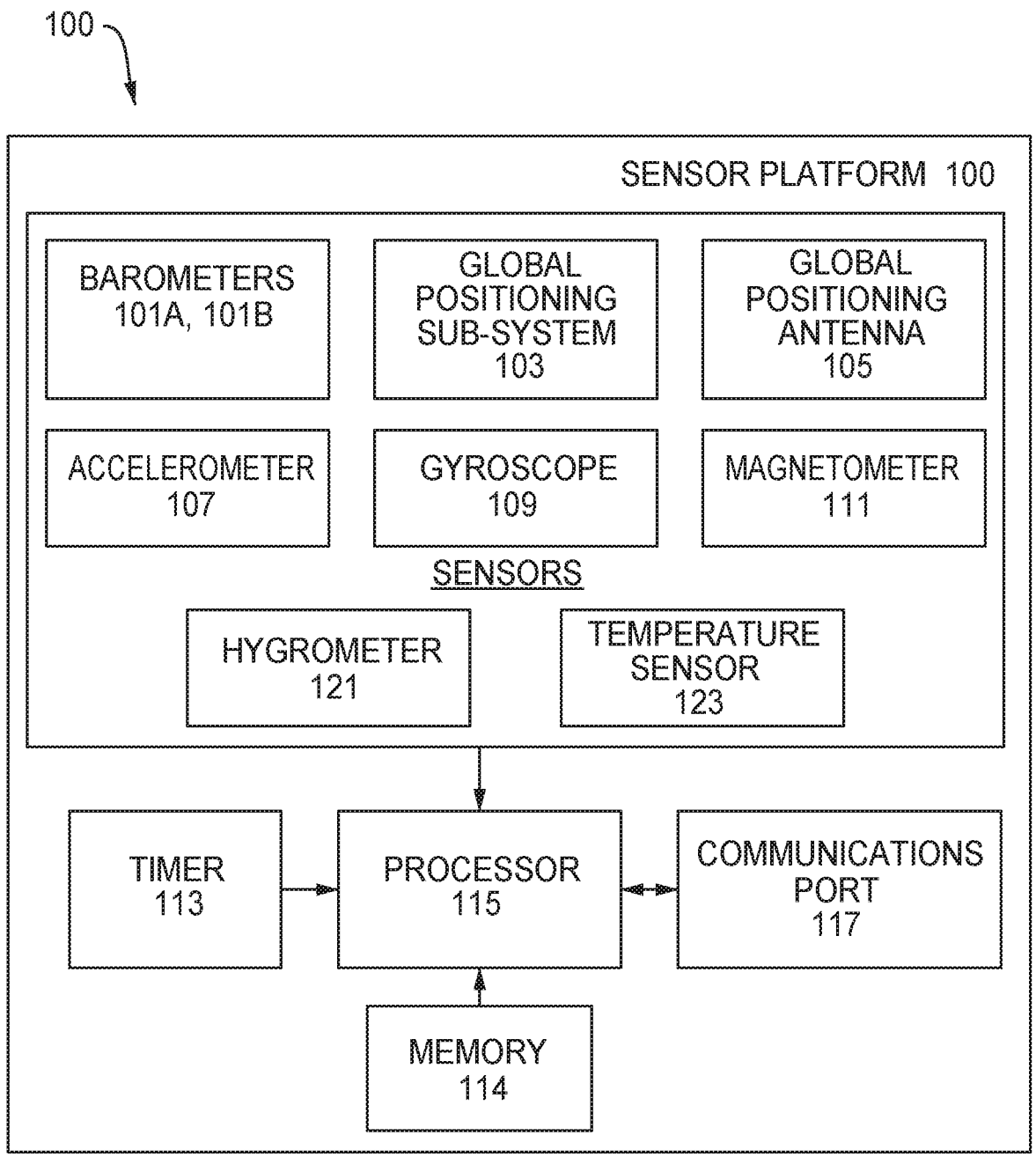
FIG. 1B is a block diagram of a sensor platform, according to some embodiments.

FIG. 1B is an example block diagram of the sensor platform 100 of FIG. 1A, in which a collection of sensors (barometer 101, Global Positioning System (GPS) subsystem 103 (e.g., including a GPS receiver), global positioning antenna 105, accelerometer 107, gyroscope 109, and magnetometer 111) and a timer 113 are electrically coupled to a processor 115, configured to send/receive signals via a communications port 117. Instead of, or in addition to, barometer 101, any other type of pressure sensor (e.g., atmospheric pressure sensor, air pressure sensor, pressure altimeter, and/or the like) can be used. The barometer 101 or other pressure sensor can measure/sense changes in pressure, for example as the user is moving. These changes in pressure can, in turn, be used by the sensing system to determine changes in the user's elevation, wind speed, running form, aerodynamics (which can change, e.g., due to changes in environmental conditions, physiological state of the user, the user's apparel/footwear, etc., over time as well as from activity to activity). The GPS subsystem 103 can acquire, via the global positioning antenna 105, a GPS signal including a user's geolocation (e.g., including latitude, longitude, altitude, and the current time). The accelerometer 107 can be a single-axis, two-axis, or three-axis accelerometer. Instead of, or in addition to, accelerometer 107, any other type of inertial measurement unit (IMU) (e.g., gyroscope, magnetometer, and/or the like) can be used. The accelerometer 107 or other IMU can measure/sense magnitude and direction of "proper acceleration" (physical acceleration), velocity, and/or orientation of a user. The gyroscope 109 (e.g., a MEMS gyroscope) can measure the orientation with respect to a fixed axis, and/or the angular velocity, of a user. The magnetometer 111 (e.g., a magnetoresistive permalloy sensor) can measure the orientation of a user with respect to the Earth's magnetic field. Since each of the accelerometer 107, the gyroscope 109, and the magnetometer 111 is capable of measuring orientation, one or more can be omitted from some designs of the sensor platform. For example, in cases where an accelerometer is being used to determine orientation, a separate gyroscope 109 and/or magnetometer 111 may not be included in the sensor platform. True net acceleration in physical space can include both linear acceleration (e.g., as measured by an accelerometer) and angular acceleration (e.g., as measured by a gyroscope). The timer 113 can provide time data (e.g., time stamps corresponding to historical measurements taken by sensors of the sensor platform 100). Time data can be stored locally (e.g., in a memory 114), used by the processor 115 for computation of one or more metrics of interest described herein, and/or transmitted via the communications port 117 (e.g., along with other measurement data derived directly from the sensors of the sensor platform 100 or stored in memory 114) to a mobile device (e.g., smart phone 102) or other remote processing device, e.g., over a communications network. In some cases, the communications port 117 includes, or is replaced by, a "data interface" which can include an antenna, an Ethernet connection, a USB port, or any other wireless or wired interface to facilitate communication (and transfer of data) between the sensor platform and a remote device (e.g., a mobile device, a communications network, etc.).

In some implementations, signal processing and feature extraction is completed via one or more algorithms running on one or more processors (e.g., processor 115). The signal processing and feature extraction can be performed partially on the sensor platform (e.g., sensor platform 100, which can be an apparel-embedded or athletic accessory-embedded portion of the sensing system) and may also be completed partially on a processing device (e.g., mobile device 102 or other device in wireless communication with the sensor platform). In other implementations, the sensor platform 100 transmits raw data (once measured/collected and/or stored in memory 114) to a remote processing device (e.g., mobile device 102 or other device in wireless communication with the sensor platform), either autonomously (e.g., according to a delivery schedule) or in response to a request received at the sensor platform from the remote processing device, for example by RF communications over a wireless communications link established by the communications port of the sensor platform, or via a wired connection (e.g., Ethernet) such that the remote processing device performs the signal processing. Information can be provided to the user (1) partially by the sensor platform and partially by a mobile device; (2) primarily or exclusively by the sensor platform (e.g., sensor platform 100); or (3) primarily or exclusively by the mobile device (e.g., mobile device 102).

A user interface and a computation device may reside within the same device, e.g., within mobile device 102, or in the sensor platform 100 itself, or may be housed separately (e.g., a computation device or processor within the sensor platform and a user interface in a mobile device, or vice-versa). A server (e.g., one or more remote servers, "the cloud," etc.) may also be used for additional analysis of data gathered by the sensor platform 100. A single server may gather data from one or more sensor platforms 100. Data may be transmitted from the sensor platform 100 to the server via a proxy, such as a computation device.

In various embodiments, a sensing system may collocate all sensors in a node, at a single sensing location. For example, the node may be an anterior measurement system located on the front of a user's foot, leg, wrist, arm, torso, head, or anterior facing location, where anterior facing corresponds to a direction of travel. This single node may include a six-axis inertial measurement unit and a pressure sensor. In some variations, the node may also include a temperature sensor and/or a humidity sensor. The single node may include at least one processor and/or memory within the node for controlling the acquisition of sensor data, storing sensor data, and/or processing sensor data.

A sensing system may distribute sensors and processing capability in one or more nodes, in standalone sensors or processors, or on external devices, such as a wearable fitness tracker or watch, a phone, a tablet, or other electronic device.

In some embodiments, the sensing system may consist of multiple components to measure the barometric pressure and/or ambient air temperature and/or relative humidity at various locations of one or more of the anterior, posterior, and/or sides of the human body. Each component may consist of one or multiple barometric pressure sensors, relative humidity, and/or ambient temperature sensors, and may or may not include kinematic sensors such as linear acceleration sensors, angular rate sensors, and/or magnetic field sensors. In some embodiments, each component may also include a processing element, storage memory, and/or data communication capabilities. These components can communicate with each other through a wired or wireless communication and transfer semi-processed intermediary sensing data or fully processed sensing data such as air pressure readings, temperature readings, and/or kinematic data.

In some embodiments, a sensing system can be a single component, configured to be placed anteriorly on the body having two pressure sensors and include an air-tight tube. The primary pressure sensor can be open to measure pressure at the anterior placed location, while the secondary pressure sensor can be connected to one end of the tube, with the other end wrapping around the body and opening at the posterior of the body. The secondary pressure sensor can thus be configured to measure the air pressure at a body surface at the posterior of the body, and the primary pressure sensor can be configured to measure air pressure at a body surface at the anterior of the body.

In another embodiment, a sensing system may consist of one or multiple components each having a pressure sensor, with components placed at multiple locations of the front, back, right side, left side, and/or or any other suitable location of the human body, and exchange measurements with each other through wired and/or wireless communication (e.g., in real-time).

Single Anterior Location Sensing Systems

In some variations, the measuring system may acquire sensor data at a single anterior location corresponding to a single region on the anterior facing side of a body in motion. Measuring sensor data at an anterior location may enable determination of air density, forces due to headwinds, crosswinds, or tailwinds, power to overcome such forces, and the power an individual needs to expend to overcome air resistance and forces due to wind from various directions. For example, the measuring system may include an anterior facing node that acquires sensed data proximate to the single node. The node may be located on the front of a user's foot, leg, wrist, arm, torso, head, in an anterior facing location, where anterior facing corresponds to a direction of travel. This node may include an inertial measurement unit (IMU) (e.g., a six-axis IMU) and a pressure sensor. In some variations, the single anterior facing node may also include a temperature sensor and/or a humidity sensor.

The single anterior facing node may include at least one processor and/or memory within the node for controlling the acquisition of sensor data, storing sensor data, and/or processing sensor data. The single anterior facing node may include a communications module for communicating with an external device, or network. The communications module may include an antenna for communicating wirelessly with an external device or network. The communications module may include an embedded interconnect for wired communication with an external device or network.

The anterior node may include a replaceable or rechargeable battery. In some variations, the single anterior node may include a wireless power receiver for charging the rechargeable battery.

Single Anterior and Single Posterior Location Sensing Systems

In some variations, the measuring system may acquire sensor data at a single anterior location and a single posterior location, for which the anterior and posterior locations correspond to single regions on the anterior facing, and posterior facing, sides of a body in motion. Anterior facing corresponds to a direction of travel, and posterior facing corresponds to the opposite direction. Measuring simultaneous anterior and posterior pressures may make it possible to measure pressure differentials due to different wind conditions. Headwinds may result in higher anterior pressures than posterior pressures, while tailwinds may result in lower anterior pressures than posterior pressures. The anterior and posterior facing nodes may be located on the anterior and posterior facing directions, respectively, of a user's foot, leg, wrist, arm, torso, head, or other part of a body in motion.

At least one of the anterior and posterior nodes may include an IMU (e.g., a six-axis IMU). The anterior and posterior nodes may each include a pressure sensor. In some variations, at least one of the anterior and posterior nodes may include a temperature sensor and/or a humidity sensor.

At least one of the anterior and posterior nodes may include at least one processor and/or memory within the node for controlling the acquisition of sensor data, storing sensor data, and/or processing sensor data. The single anterior facing node may include a communications module for communicating with an external device, another node, or a network. The communications module may include an antenna for communicating wirelessly with an external device, another node, or a network. The communications module may include an embedded interconnect for wired communication with another node, an external device or a network.

The anterior and/or posterior node may include a replaceable or rechargeable battery, for charging the node containing the battery. In some variations, the anterior and/or posterior node may include an embedded power interconnect for charging another node. In some variations, the anterior and/or posterior node may include a wireless power receiver for charging the rechargeable battery in that node.

Multiple Anterior Location Sensing Systems

In some variations, the measurement system may acquire sensor data at more than one location on the anterior facing side of a body in motion. Acquiring sensor data at multiple locations make it possible to quantify pressure differentials due to crosswinds, as, for example pressures may be higher on the right side of a torso than the left side of a torso, if a crosswind is coming from the right side of a direction of travel. The anterior locations for acquiring data may include left and right feet or legs; left, right, upper, lower, and/or central torso; left and/or right wrist; and left, central, or right head location.

There are multiple sensor configurations for capturing pressure sensor data from these multiple locations. In some variations two or more nodes with pressure sensors may acquire pressure sensor data at corresponding locations on the anterior side of a body in motion. In other variations, one or more nodes, and one or more sensors, may acquire pressure sensor data at corresponding locations on the anterior side of a body in motion.

In some variations, a node may include an embedded pressure tube that extends from the pressure sensor to another location in order to acquire pressure data at that other location. For example, a node may include a first pressure sensor that acquires sensor data at the node, and a second pressure sensor coupled to the embedded pressure tube to acquire pressure at the other location. This makes it possible for a pressure sensor within a node to acquire pressure data at a location distal to the node, by extending a pressure tube from the node to the distal location. For example, a node on the left side of a torso may include a pressure tube that extends to the right side of the torso, so that pressure sensors in the node on the left side of the torso may simultaneously acquire pressure data on the left and right sides of the torso. Similarly, sampling tubes may be extended to other locations on the anterior side of a body in motion, to locations on the posterior side of the body in motion, or other surface locations of the body in motion.

Each pressure sensor in a node, or standalone, may or may not be accompanied by other sensors, such as a temperature sensor, a humidity sensor, an inertial measurement sensor, or another sensor. The one or more anterior nodes and/or sensors may communicate control instructions, sensor data, or processed sensor data, via wired communications to other nodes, sensors, or an external device. In some variations, the one or more anterior nodes may include a temperature sensor and/or a humidity sensor.

The one or more anterior nodes may include at least one processor and/or memory within the node for controlling the acquisition of sensor data, storing sensed data, and/or processing sensed data. The one or more anterior nodes may include a communications module for communicating with an external device, another node, or a network. The communications module may include an antenna for communicating wirelessly with an external device, another node, a sensor, a sensor, or a network. The communications module may include an embedded interconnect for wired communication with one or more sensors in the node, another node, an external device or a network.

The one or more anterior nodes and/or standalone sensors may include a replaceable or rechargeable battery, for charging the node containing the battery. In some variations, the one or more anterior nodes and/or standalone sensors may include an embedded power interconnect for charging another node. In some variations, the one or more anterior nodes and/or standalone sensors may include a wireless power receiver for charging the rechargeable battery in that node.

Multiple Anterior and Posterior Location Sensing Systems

In some variations, the measurement system may acquire sensor data at more than one location on the anterior facing side of a body in motion, and at more than one location on the posterior facing side of a body in motion. Acquiring sensor data at multiple locations make it possible to quantify pressure differentials due to crosswinds, as, for example pressures may be higher on the right side of a torso than the left side of a torso, if a crosswind is coming from the right side of a direction of travel, as well as measuring pressure differences between anterior and posterior sides of a body in motion. The anterior and posterior locations for acquiring data may include left and right feet or legs; left, right, upper, lower, and/or central torso; left and/or right wrist; and left, central, or right head location.

There are multiple sensor configurations for capturing pressure sensor data from these multiple locations. In some variations two or more nodes with pressure sensors may acquire pressure sensor data at corresponding locations on the anterior side, and the posterior side, of a body in motion. In other variations, one or more nodes, and one or more sensors, may acquire pressure sensor data at corresponding locations on the anterior side, and the posterior side, of a body in motion.

In some variations, a node may include an embedded pressure tube that extends from the pressure sensor to another location in order to acquire pressure data at that other location. For example, a node may include a first pressure sensor that acquires sensor data at the node, and a second pressure sensor coupled to the embedded pressure tube to acquire pressure at the other location. This makes it possible for a pressure sensor within a node to acquire pressure data at a location distal to the node, by extending a pressure tube from the node to the distal location. For example, a node on the left side of a torso may include a pressure tube that extends to the right side of the torso, so that pressure sensors in the node on the left side of the torso may simultaneously acquire pressure data on the left and right sides of the torso. Similarly, sampling tubes may be extended to other locations on the same side of a body in motion, to locations on the other side of the body in motion, or other surface locations of the body in motion.

Each pressure sensor in a node, or standalone, may or may not be accompanied by other sensors, such as a temperature sensor, a humidity sensor, an inertial measurement sensor, or another sensor. The one or more anterior nodes and/or sensors may communicate control instructions, sensor data, or processed sensor data, via wired communications to other nodes, sensors, or an external device. In some variations, the one or more anterior nodes may include a temperature sensor and/or a humidity sensor.

The one or more anterior nodes may include at least one processor and/or memory within the node for controlling the acquisition of sensor data, storing sensed data, and/or processing sensed data. The one or more anterior nodes may include a communications module for communicating with an external device, another node, or a network. The communications module may include an antenna for communicating wirelessly with an external device, another node, a sensor, a sensor, or a network. The communications module may include an embedded interconnect for wired communication with one or more sensors in the node, another node, an external device or a network.

The one or more anterior nodes and/or standalone sensors may include a replaceable or rechargeable battery, for charging the node containing the battery. In some variations, the one or more anterior nodes and/or standalone sensors may include an embedded power interconnect for charging another node. In some variations, the one or more anterior nodes and/or standalone sensors may include a wireless power receiver for charging the rechargeable battery in that node.

Sensor Platforms

Figure 2A:
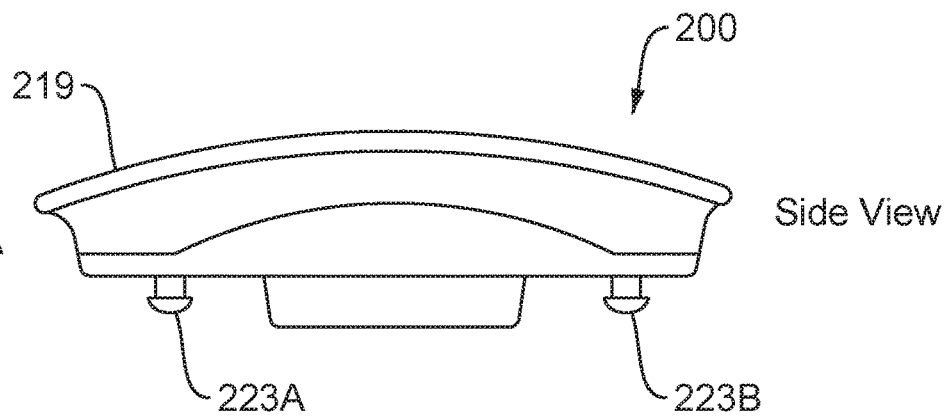
FIGS. 2A-2D are renderings of a sensor platform, according to some embodiments.
Figure 2B:
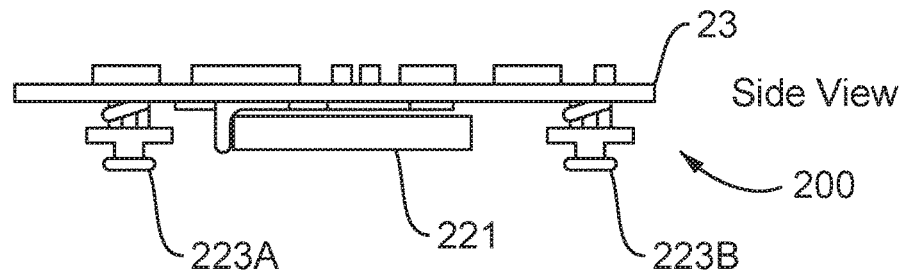
Figure 2C:
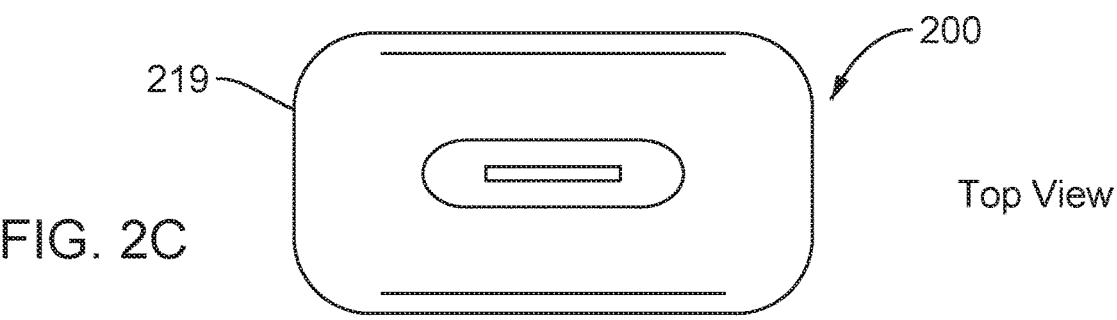
Figure 2D:
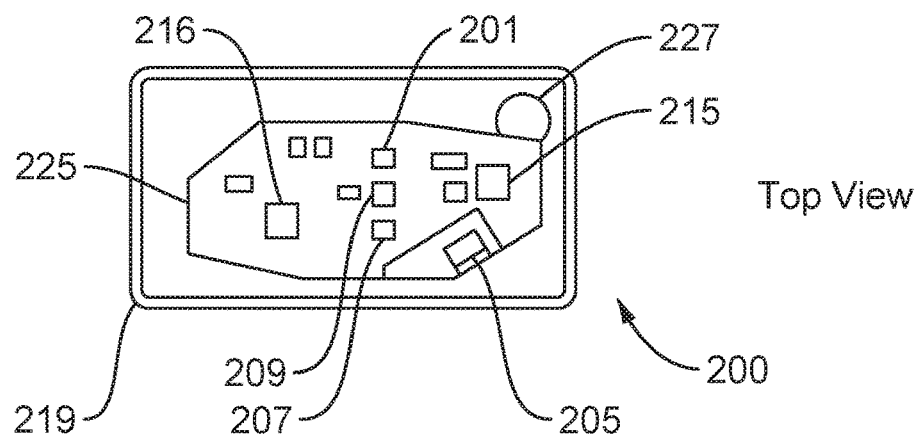

FIGS. 2A-2D are renderings of a sensor platform 200, according to some embodiments. The sensor platform 200 can be used, for example, as part of a sensing system (e.g., as sensor platform 100 in FIG. 1A). FIG. 2A is a side view of an assembled sensor platform 200, in which an enclosure or "housing" 219 and two metal snaps 223A, 223B are visible. FIG. 2B is a side view of a partially disassembled sensor platform 200, in which a battery 221 and two metal snaps 223A, 223B are visible. FIG. 2C is a top view of an assembled sensor platform 200, showing enclosure 219. FIG. 2D is a top view of a partially disassembled sensor platform 200, in which a portion of the enclosure 219, a printed circuit board 225, a vent 227, an accelerometer 207, a gyroscope 209, a barometer 201, a microcontroller (or "processor") 215 operably coupled to a memory 216, and an antenna 205 are visible. The metal snaps 223A, 223B can be used to mechanically and/or electrically couple the sensor platform 200 to a garment (e.g., a shirt, shorts, arm band, leg band, shoe, etc.) or an accessory (e.g., a chest strap, arm band, leg band, watch, wrist band. bracelet, and/or the like) so that the sensor platform 200 is in close proximity with, or in contact with, the user's body. The sensor platform may be worn by any animal, such as a human.

In some examples, the processor 215 is configured to: (1) translate multi-axis motion data, using orientation data (e.g., measured by the accelerometer 207 and/or the gyroscope 209), from the reference frame fixed with respect to the housing 219 to a reference frame fixed with respect to the Earth so as to yield translated multi-axis motion data; (2) decompose the translated multi-axis motion data into horizontal motion components and vertical motion components in the reference frame fixed with respect to the Earth; and (3) estimate power expended by the user based on the horizontal motion components and the vertical motion components.

The memory 216 can store previously measured multi-axis motion data, and the processor 215 can be configured to vary the first sampling rate based on a comparison of the motion data to the previously measured multi-axis motion data.

The sensor platform 200 or sensing system (e.g., of FIG. 1A) can include one or more pressure sensor (e.g., an atmospheric pressure sensor or air pressure sensor), such as a barometer, operably coupled to a processor. For example, as shown in the sensor platform 200 of FIG. 2D, barometer 201 is operably coupled to the processor 215 via PCB 225, to measure changes in pressure experienced by the system due to variations in altitude and/or wind resistance.

Alternatively or in addition, the sensor platform or sensing system can include a Global Positioning System (GPS) receiver (e.g., of GPS subsystem 103 in FIG. 1A), operably coupled to the processor 215, to receive a GPS location signal representing a location of the system. The sensor platform 200 can also include a flexible potting compound (see, e.g., discussion of FIG. 4 below), disposed within the housing 219, to reduce mechanical stress experienced by at least one of the housing 219, the IMU (e.g., accelerometer 207), and the orientation sensor (e.g., gyroscope 209), and/or other components of the sensor platform 200 whose performance can be affected by excessive mechanical stress, e.g., due to impact forces during running, vibration, etc.

Figure 3A:
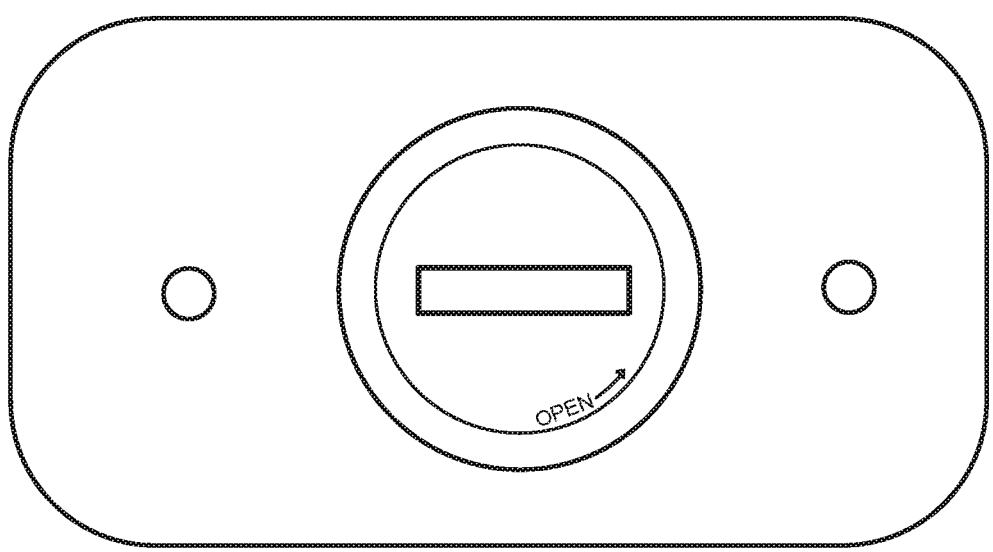
FIGS. 3A and 3B are renderings of top and bottom views, respectively, of an assembled sensor platform, device according to some embodiments.
Figure 3B:
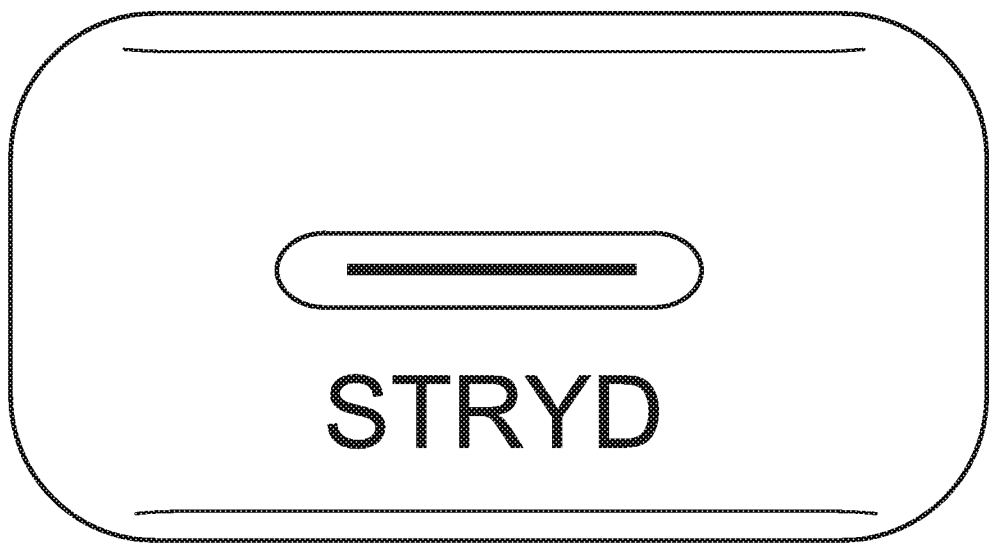
Figure 3C:
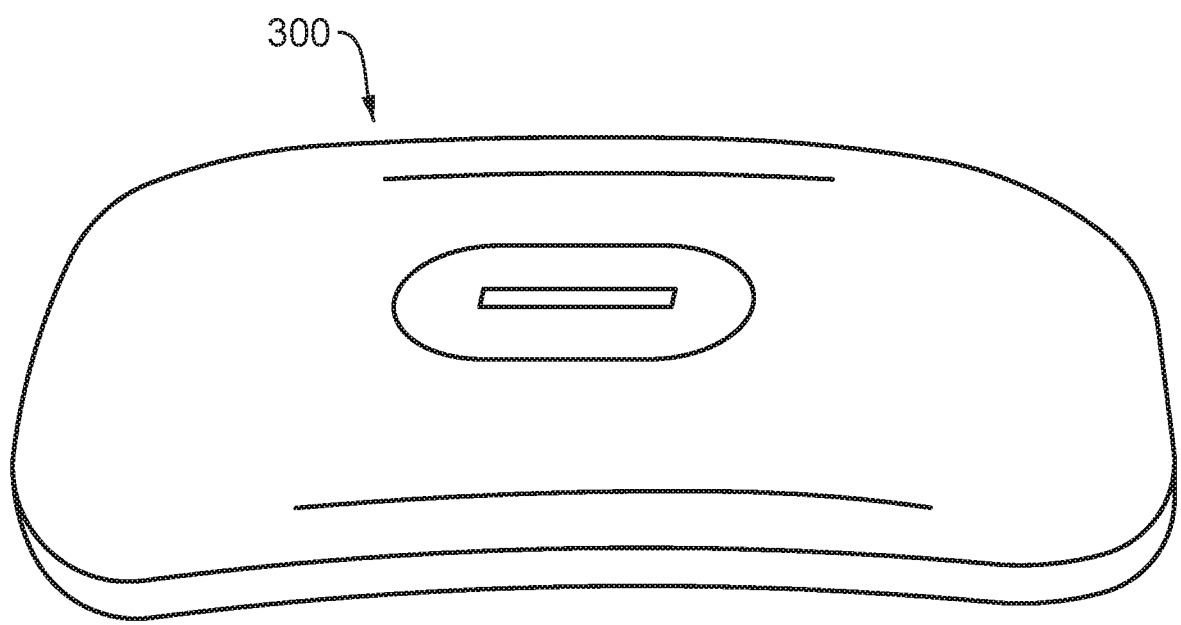
FIG. 3C is a rendering of a top perspective view of the assembled sensor platform of FIGS. 3A and 3B.

FIGS. 3A and 3B are renderings of top and bottom views, respectively, of an assembled sensing platform 300 according to some embodiments, and FIG. 3C is a rendering of a top perspective view thereof. The sensor platform 300 can be used, for example, as part of a sensing system (e.g., as sensor platform 100 in FIG. 1A). As shown in FIG. 3A, the sensing platform enclosure or housing can include a replaceable cover coupled (e.g., threadably) to the housing, that a user can rotate for removal, e.g., to allow the user access to the internal power source (e.g., a coin cell battery) for replacement. The profile of the sensing platform housing, as shown in FIGS. 3A-3C, can have a smooth, contoured profile and compact form factor to facilitate integration into a wearable electronics garment and/or for attachment to a garment or accessory. Two holes (shown in FIG. 3A) can be provided for mechanical and/or electrical attachment to the garment or accessory (e.g., via snap engagement).

Figure 4:
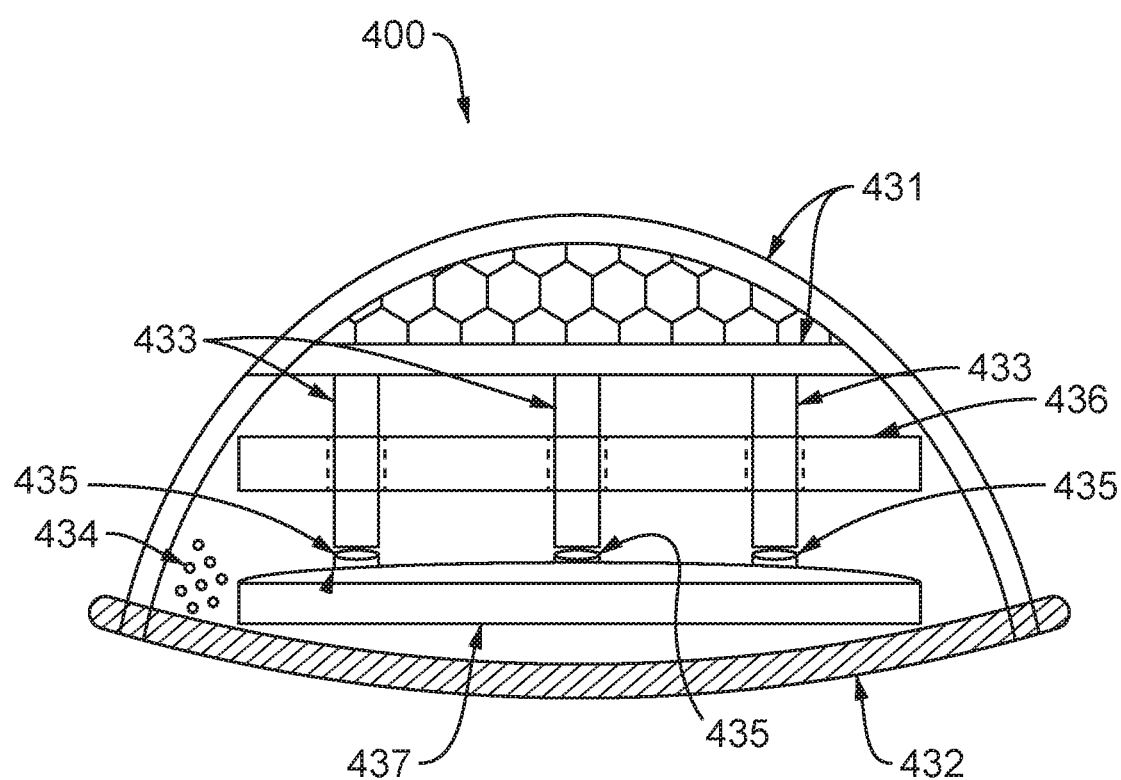
FIG. 4 shows a sensor device enclosure for harsh environments, according to some embodiments.

FIG. 4 shows a sensor platform 400 with an enclosure (also referred to herein as a "housing" or "package") for harsh environments, according to some embodiments. The sensor platform 400 can be used, for example, as part of a sensing system (e.g., as sensor platform 100 in FIG. 1A). In some implementations, the enclosure of the sensor platform 400 may be embedded in a piece of apparel (e.g., in an athletic shoe, a shirt, shorts, etc.) or an athletic accessory (e.g., a chest strap, arm band, leg band, wrist band, headband, watch, smartphone, dongle, and/or the like) that is, or will be during use, subject to high forces, and as such may include one or more features (such as those shown in FIG. 4) to promote durability and/or to protect the embedded electronics of the sensor platform 400.

The sensor platform enclosure can be a high-performance, robust enclosure for protecting embedded electronics. For example, the sensor platform 400 enclosure as shown in FIG. 4 includes an arched top 431, a reinforced bottom plate 432, a plurality of weight distribution pillars 433 to distribute forces (e.g., impact, vibration, etc.) experienced by the sensor platform, a flexible potting compound 434, a plurality of shock absorbers 435 each disposed at an end of a corresponding weigh distribution pillar, a printed circuit board (PCB) 436, and a battery 437 (e.g., a coin cell battery).

The density of the enclosure (e.g., including arched top 431 and/or bottom plate 432), in some embodiments, is designed so as not to exceed the density of the surrounding shoe materials, thereby adding little or no extra weight as compared with a shoe without embedded circuitry. In some embodiments, the enclosure size is kept small while increasing or maximizing structural support to provide high performing load-bearing and shock-absorption capabilities.

As described herein, a system for measuring motion of a user during physical activity can include a housing and an inertial measurement unit (IMU) disposed within the housing to acquire multi-axis motion data at a first sampling rate. In such cases, the multi-axis motion represents motion of the system in a reference frame fixed with respect to the housing. An orientation sensor (e.g., an accelerometer, gyroscope, or magnetometer) is also disposed within the housing, and configured to acquire orientation data at a second sampling rate. In some cases, the IMU itself (e.g., when the IMU is an accelerometer) serves as an orientation sensor by sensing the direction of weight changes of the user. The orientation data represents an orientation of the system, for example with respect to the Earth. A processor is disposed within the housing and operably coupled to the IMU and to the orientation sensor, to vary the second sampling rate based on the multi-axis motion data. A memory, disposed within the housing and operably coupled to the processor, is configured to store the multi-axis motion data and the orientation data. A data interface, operably coupled to the processor, is configured to transmit the multi-axis motion data and the orientation data to another computing device.

In some configurations, the orientation sensor comprises a gyroscope. The memory can store previously measured multi-axis motion data, and the processor can be configured to vary the second sampling rate based on a comparison of the multi-axis motion data to the previously measured multi-axis motion data. The processor can also be configured to (i) estimate when the user is airborne based on the multi-axis motion data and (ii) disable the gyroscope when the user is airborne.

Figure 10:
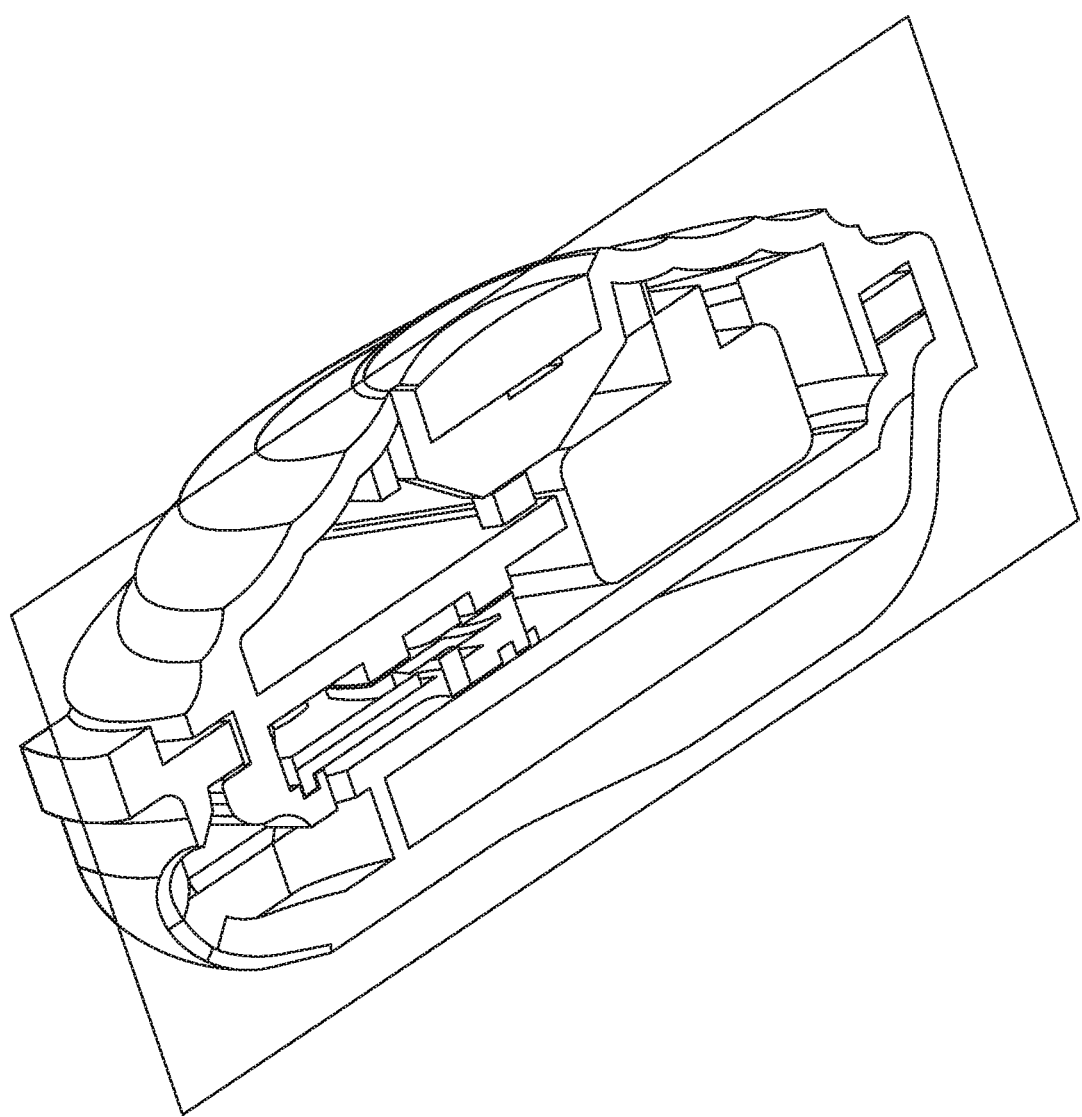
FIG. 10 shows the structural design of a sensor node, including a pressure chamber and equalization membrane, and a clip with a wind port and chamber
Figure 11:
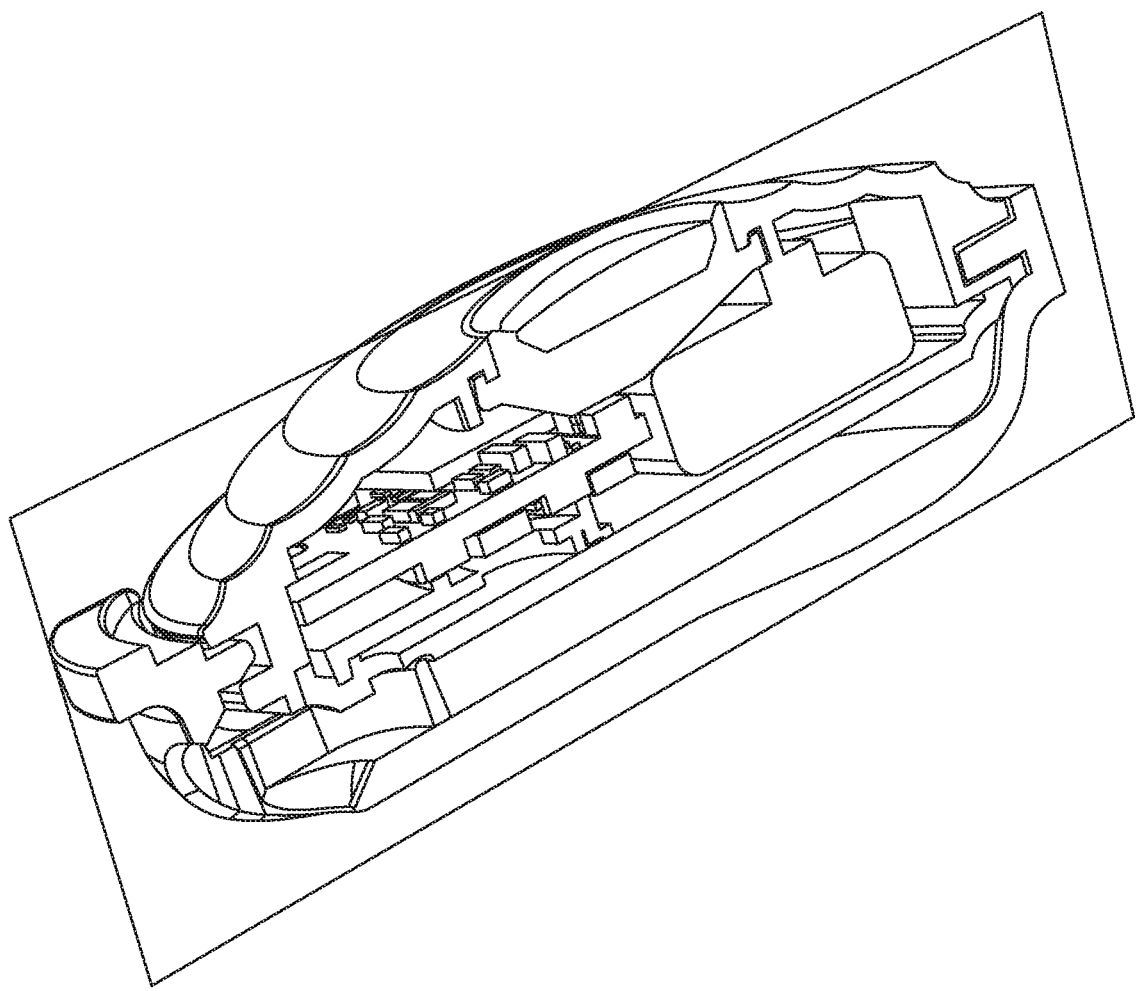
FIG. 11 shows the sensor node of FIG. 10, with an external chamber formed by the combined bottom portion of the shell and the clip structure.

FIG. 10 shows the structural design of a sensor node, including a pressure chamber and equalization membrane, and a clip with a wind port and chamber FIG. 11 shows the sensor node of FIG. 10, with an external chamber formed by the combined bottom portion of the shell and the clip structure.

Figure 12:
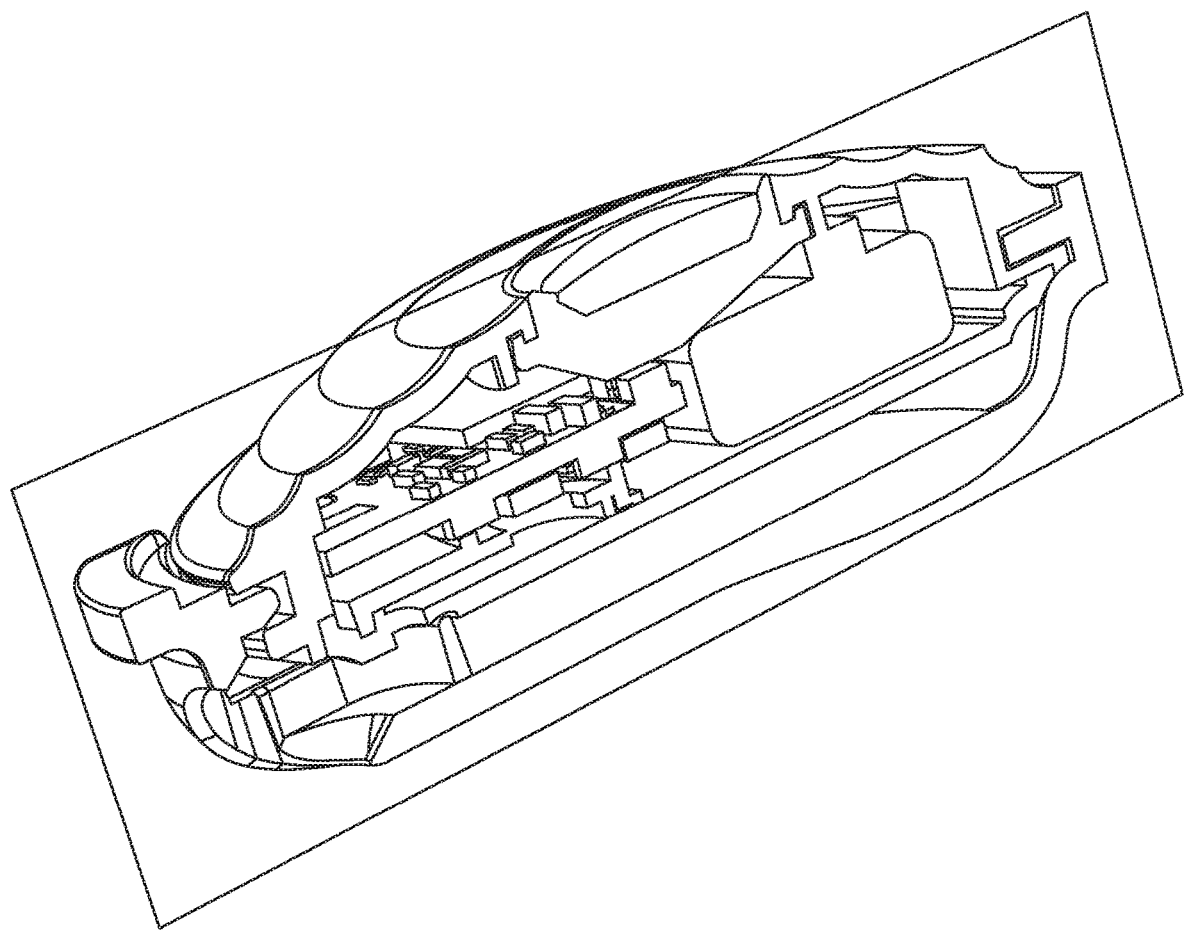
FIG. 12 shows an internal chamber formed by the combined bottom portion of the shell and an interior chamber wall.

FIG. 12 shows an internal chamber formed by the combined bottom portion of the shell and an interior chamber wall.

Use of the Wearable Sensor Platform

Figure 5:
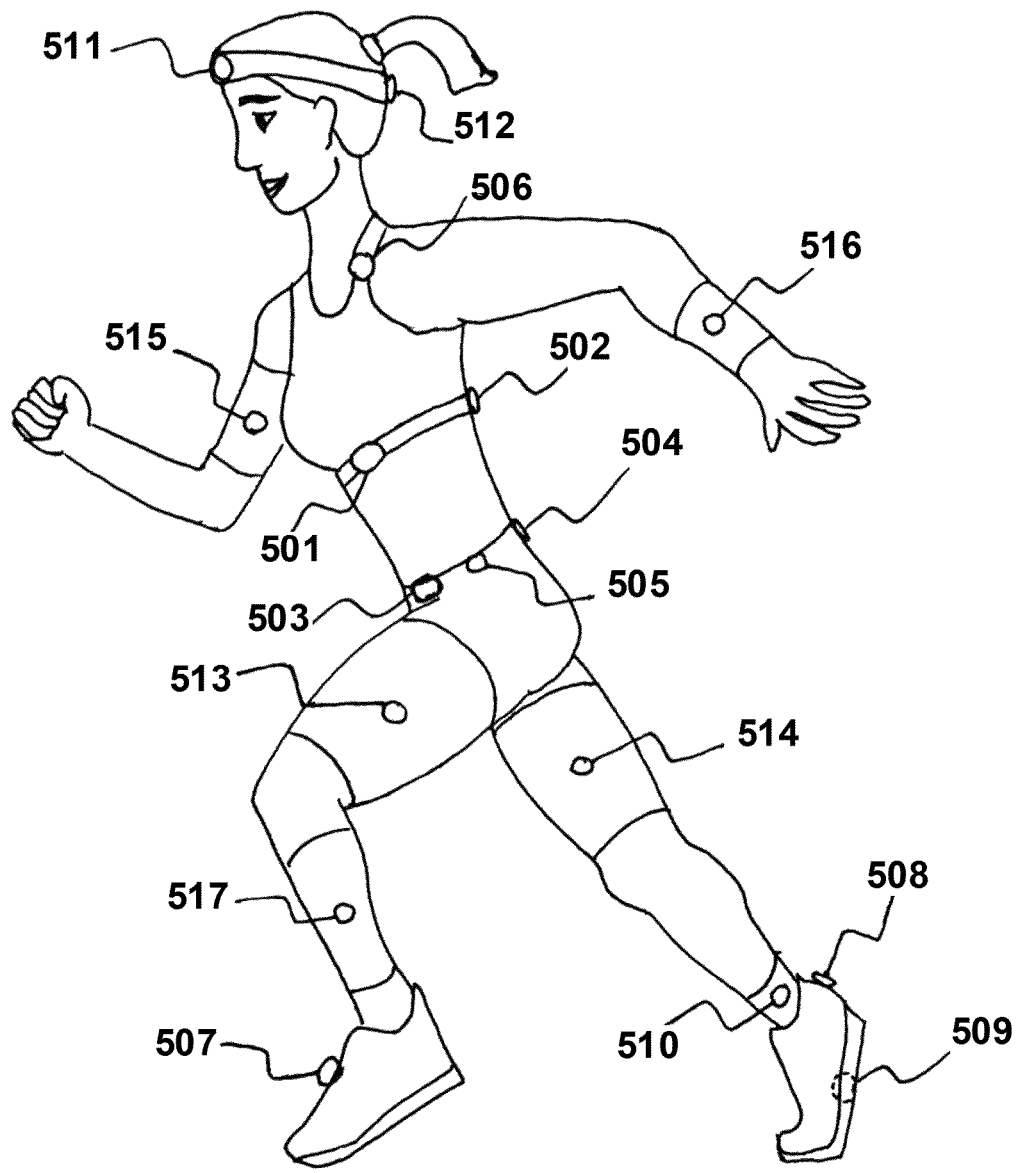
FIG. 5 shows the placement of components of a sensing system on a user, according to some embodiments.

During use, a user affixes a sensor platform as described herein (e.g., sensor platform 100 of FIG. 1A) to a surface of, or in close proximity to, their body (e.g., secured by a chest strap, wrist strap, leg band, etc.) and conducts a physical activity such as walking, running, dancing, and/or the like. By way of example, the sensor platform (e.g., including one or more inertial measurement units, an orientation sensor, and an optional barometer) may be placed on various locations of the body, for example, at the following locations, as shown in FIG. 5: on the front 501, back 502, or side of the torso, on the front 503, back 504, or side 505 of the waist, embedded in clothing 506, attached to (507, 508) or embedded within (509) one or both shoes, on one or both socks 510, on the front 511 or back 512 of a headband, on one or both thighs (513, 514), in one or both arm bands (515, 516), or on one or both calves 517. Depending upon the implementation, each location can have one or more of the following advantages: (a) convenience to the user, (b) accuracy of measuring running and/or walking technique and distance, (c) accuracy in measuring the geographic position of the user, (d) improved sensed data quality, (e) improved user comfort, (f) monitoring of one or more limbs of a user; and (f) reduced stress on the sensing device. By way of example, beneficial locations can include within or on a strap attached to the ankle, leg, wrist, waist, or torso. The sensor platform can also be placed within or on apparel such as clothing, belts, or shoes. It can also be placed on, under, or to the side of the foot.

The sensor platform can include a user interface (e.g., including an electronic display, touchscreen, pushbuttons, dials, indicator light(s), speaker(s), microphone(s), keyboard, etc.), for example to allow users access to information about metrics and maps described herein. In some embodiments, the user interface functionality is divided between/among the sensor platform, and software running on a mobile device (e.g., commodity or special-purpose devices, such as smartphones) that communicates with the sensor platform. In some embodiments, the user interface functionality resides within a mobile device. In some embodiments, the user interface functionality resides within the sensor platform. The device that contains the user interface (e.g., the mobile device 102 and/or the sensor platform 100 of FIG. 1A) may be called an "interface device."

The sensor platform can provide feedback to a user in audio-visual form during use. The sensor platform and user interface can provide off-line and real-time information to the users. The real-time information can be easy to access, and accessible during physical or mental activity. For example, a compact colored light on the sensor platform, or audio output from the user interface, may be used to indicate information to a user. In some embodiments, the off-line information is organized to allow users to vary the level of detail and type of information displayed. For example, users may scroll through a map or timeline of activities to see detailed information about metrics of interest for different times and locations. The system may also be prompted to provide information of interest that did not originate in the sensor platform, e.g., metrics of interest from other users, the time, and personal information stored on the interface device (e.g., a smartphone).

Feedback Triggering

The sensor platform and/or interface device can provide active and/or passive feedback to the users. Active feedback has the potential to distract the user from physical or mental activities, and can be presented on a schedule chosen by the user, when explicitly requested, or when determined to be valuable due to values or patterns in metrics of interest. Users may explicitly request active feedback through actions that require little deviation from their ongoing activities, e.g., by a gesture such as tapping a foot, changing the angle of a limb, or tensing a particular muscle.

Wearable Sensor Platform—Motion Measurements

The mechanical power output of the human body is a function of the velocity and the forces of and on the various parts of the body. In some embodiments, to enable accurate estimation of person and/or limb motion, location, and/or orientation in a compact, low-power package, the activation(s) of an inertial measurement unit (e.g., an accelerometer, such as a three-axis accelerometer), a gyroscope and/or magnetometer, a pressure sensor, and/or a GPS is/are controlled, and their measurements are combined. These components can be integrated within a compact sensing platform (e.g., equipped with a microcontroller) and a wireless communication interface. Computation and sensing can be carried out entirely on a microcontroller in the sensor platform, or some or all computation and/or sensing can be offloaded to a remote device such as a smartphone. The entire sensing system, including the sensor platform and communicating external hardware and software, is herein referred to as the "sensing system."

Depending upon the embodiment, the disclosed sensing system includes one or more of the following capabilities: (1) determine the motion, positions, and orientations of one or more parts of the body of a user wearing the sensor platform, (2) use gathered/sensed data to carry out detailed, and in some embodiments comparative, time-dependent gait analysis of one or more limbs, (3) determine the incline of the user's path, (4) determine the impact of wind on human speed and forces, (5) measure the passage of time, (6) use general physical properties of bipedal motion and a combination of the data described in the above items to determine instantaneous body velocity, force, and the passage of time (thereby allowing power expenditure to be calculated), and (7) control the activities of sensing system components such as sensors (e.g., one or more inertial measurement units, accelerometers, gyroscopes, temperature sensors, inertial sensors, force sensors, pressure sensors, Global Positioning System (GPS) receivers, flex sensors, etc.), processors, wireless communication transceivers, and/or display elements, to reduce or minimize power consumption.

Multiple sensors can provide data allowing person and limb position, motion, and orientation to be estimated. Some of these sensors have higher power consumptions than others when activated. One relatively low power sensor is the inertial measurement unit (IMU, e.g., an accelerometer).

IMU data acquisition: Acceleration samples can be gathered by the IMU (e.g., an accelerometer) at a variable frequency that is adjusted based on the current accuracy and power consumption requirements. These data represent acceleration as viewed from the reference frame of the sensor. However, they may not represent acceleration as viewed form the reference frame of the Earth.

In some instances, IMUs do not allow orientation to be estimated. Therefore, an inertial measurement unit can, in some embodiments, be combined with a magnetometer or gyroscope for orientation estimation. Of these two sensors, magnetometers generally have lower power consumptions.

Reference frame translation: Gyroscope and/or magnetometer samples may be gathered at a variable frequency that is adjusted based on the current acceleration and power consumption requirements. These data may be used to determine the changes in orientation of the sensor relative to the direction of gravity or some part of the user's body. This information may be used, for example, to translate the accelerometer data from its reference frame to the reference frame of the Earth. Some environments, such as indoor environments where large pieces of ferrous metal are present, can interfere with magnetometer use for orientation estimation. In scenarios where magnetometer readings are unreliable, e.g., inconsistent with gyroscope readings, a gyroscope may be used instead.

Over time, measurement error can cause absolute gyroscope orientation readings to accumulate error, thereby producing an absolute orientation that may be inconsistent with reality. In some embodiments, to prevent error accumulation over long time durations, the orientation may be recalibrated with each step. For example, for an embodiment in which the sensing platform is attached to the foot, gyroscope and/or accelerometer readings are used to determine when the foot is placed flat on the ground. The ground angle can be estimated using position and topographical data, or measured using the accelerometer. A proportional integral derivative (PID) algorithm may be used to recalibrate the gyroscope to reduce or minimize the error between the angle measured by the gyroscope and that determined through other means. When the foot leaves the ground, the PID algorithm can be disabled and the gyroscope can be used to measure the angle of the foot until it is again in contact with the ground. The presence of the foot on the ground may be detected by determining when all of the following are true: (1) The downward acceleration is approximately 9.8 m/s² (note that a different estimation approach may also be used, in which the foot is determined to be on the ground when the length of the vector given by a multi-access accelerometer is approximately 9.8 m/s²); (2) The change in angle over last 50 milliseconds is approximately zero; (3) Foot impact, as detected with an accelerometer, occurred approximately 300 ms prior.

In some embodiments, as a body part (e.g., a limb) rotates, the 3 axis accelerometer reading can be multiplied (e.g., via a processor on board the sensor platform and/or via a remote processor on a mobile device or other device in wireless communication with the sensor platform) by a rotation matrix in order to determine which direction the person is facing.

$$\begin{bmatrix} acc'_x \\ acc'_y \\ acc'_z \end{bmatrix} = \begin{bmatrix} \cos\theta & 0 & \sin\theta \\ 0 & 1 & 0 \\ -\sin\theta & 0 & \cos\theta \end{bmatrix} \times \begin{bmatrix} acc_x \\ acc_y \\ acc_z \end{bmatrix}$$

where $acc_x$, $acc_y$, and $acc_z$ are readings from the three-axis accelerometer, $acc'_x$, $acc'_y$, and $acc'_z$ are the orientation-compensated readings from the three-axis accelerometer, and $\theta$ is the angle measured by the gyroscope. This approach may also be used with the gyroscope being replaced by a magnetometer.

Pressure measurements: A pressure sensor (e.g., an atmospheric pressure sensor, air pressure sensor, barometer, pressure altimeter, and/or the like) can be included in the sensor platform used to detect changes in a user's elevation (i.e., attitude or vertical position). Filtering (e.g., low-pass filtering with a cutoff frequency of ~0.2 Hz, or band-pass filtering with a range of ~0.1 Hz-~ 0.3 Hz) of the pressure sensor signal can also be used to compensate for air that is incident on the runner (e.g., strong winds, puffs of air, abrupt changes in wind patterns, and/or other aerodynamic factors that cause rapid pressure changes, any of which may vary with time, location, running form, body/limb positioning of the user, and/or other factors) so that the signal is more stable and/or relates primarily to the user's altitude. In some cases where a pressure signal is filtered, the cutoff frequency can be changed dynamically to account for changes in a runner's attitude.

In some cases, the forward motion of a person can be estimated accurately without the use of GPS, and are designed to mitigate or avoid high power consumption and short battery lifespans for the sensing platform. In some embodiments, to avoid frequent activation of a high power consumption gyroscope, a sampling technique is used. A sampling technique in which the gyroscope is deactivated for a subset of paces can result in accumulation of motion and position error for those paces. To reduce or eliminate such errors, an adaptive sampling technique can be used, in which the gyroscope is reactively activated when there is a significant difference between the time-varying multi-axis accelerometer data for that pace and a library of accelerometer data from (not necessarily all) prior paces. When the accelerometer data are similar to those from a prior pace, the gyroscope-enhanced motion estimates from that pace can be used. Accelerometer pace data may be compressed via curve fitting. A subset of paces will have their data stored, with a size limited by available memory and comparison overhead. Heuristics, e.g., based on variation in pace and/or cadence, may be used to make the search for matching prior pace accelerometer data faster.

Although the described position, motion, and orientation estimation technology described is generally quite accurate, some small amount of error can accumulate over long time intervals. Therefore, if a GPS receiver is available, it may be infrequently activated to correct accumulated position estimation error. An inertial measurement unit, magnetometer, gyroscope, and GPS receiver (or subset thereof) can thus be used together, in some embodiments, to accurately estimate person and limb position, motion, and orientation with minimal energy consumption.

In some examples, e.g., to achieve improved accuracy for physiological and/or motion-related measurements, low-frequency measurements can be used to classify activity. For example, a power efficient accelerometer can be used in a low-frequency, low-power sampling mode to classify activity, e.g., walking or running. In some such embodiments, the sensing system can transition to a higher-frequency, higher-power mode, for example when an activity meriting such a transition is detected, e.g., running. In other words, high-frequency measurements can be made when appropriate for the current activity. This transition can be automated, thus requiring no command from, or explicit interaction with, the user. Even in the higher-frequency sampling mode, local data processing can be used to extract relevant and compact features, which can in turn be transmitted to external devices at lower energy cost than the raw measured data. A Fourier transform can be applied to the raw data gathered at low sampling frequency, either on the sensor node or on an external device, allowing temporal features to be detected with high accuracy. Different methods of analysis can also be applied at different sampling frequencies. For example, at low sampling frequency, frequency-domain analysis can be used, and at high sampling frequency, time-domain analysis can be used. This technique facilitates transition among sensing modes with different temporal resolutions and power consumptions without explicit commands or interaction with the user. This achieves a good trade-off between computational/energy cost and feature extraction accuracy.

To estimate change in speed in distance over time with low energy use, contextual information, such as measured stride length for a particular set of physiological and motion-related metrics, can be used together with measurement of motion-related metrics.

Drift compensation: Multiple sensors are capable of providing data allowing person and limb position, motion, and orientation to be estimated. Some of these sensors have higher power consumptions than others when activated. One relatively low power sensor in the inertial measurement unit is typically an accelerometer. However, inertial measurement units typically do not allow orientation to be estimated. Therefore, an inertial measurement unit can, in some embodiments, be combined with a magnetometer or gyroscope for orientation estimation. Of these two sensors, magnetometers generally have lower power consumptions. If feasible for a given implementation, the magnetometer can be used in combination with the accelerometer. However, some environments such as indoor environments where large pieces of ferrous metal are present, can interfere with magnetometer use for orientation estimation. In scenarios where magnetometer readings are unreliable, e.g., inconsistent with gyroscope readings, a gyroscope may be used instead. Although the described position, motion, and orientation estimation technology is generally quite accurate, some small amount of error can accumulate over long time intervals. Therefore, if a GPS receiver is available, it may be infrequently activated to correct accumulated position estimation error. In summary, an inertial measurement unit, magnetometer, gyroscope, and GPS receiver (or subset thereof) can be used together to accurately estimate person and limb position, motion, and orientation with minimal energy consumption.

Techniques described herein allow for the accurate estimation of motion, orientation, and position of a person's limb over time, over both long and short distance scales using a compact device with long battery life. In some embodiments, an IMU, combined with a gyroscope, may be used to determine the orientation of a limb is described first. In some implementations, human feet are the body parts for which position and orientation are measured. Data collected by the sensor platform may be used to estimate the coarse-grained location of the person. They may also be used to track the paths and orientations of limbs during athletic activities such as running or swinging a baseball. Orientation-corrected accelerometer readings can be integrated over time (e.g., using a processor disposed within the sensor platform or within a mobile device in wireless communication with the sensor platform) to determine a three-dimensional path of the limbs being monitored by sensing platforms.

In some embodiments, a method of measuring motion of a user during physical activity is performed using a system comprising an inertial measurement unit (IMU) and an orientation sensor disposed within a housing. The method includes: (1) acquiring multi-axis motion data with the IMU at a first sampling rate, where the multi-axis motion represents motion of the housing in a reference frame fixed with respect to the housing; (2) acquiring orientation data with the orientation sensor at a second sampling rate, where the orientation data represents an orientation of the housing with respect to the Earth; and (3) varying the second sampling rate based on the multi-axis motion data. Varying the second sampling rate can include comparing the multi-axis motion data to previously measured multi-axis motion data. Alternatively or in addition, varying the second sampling rate includes estimating when the user is airborne based on the multi-axis motion data, and disabling the orientation sensor when the user is airborne.

An example of a method includes: (1) translating the multi-axis motion data, using the orientation data, from the reference frame fixed with respect to the housing to a reference frame fixed with respect to the Earth so as to yield translated multi-axis motion data; (2) decomposing the translated multi-axis motion data into horizontal motion components and vertical motion components in the reference frame fixed with respect to the Earth; and (3) estimating power expended by the user based on the horizontal motion components and the vertical motion components. The method can include varying the first sampling rate based on a comparison of the multi-axis motion data to previously measured multi-axis motion data. The method can also include measuring changes in pressure experienced by the system due to variations in altitude and/or wind resistance.

Sensing System—Transferring Data to a Mobile Device

A sensing platform as described herein (e.g., sensor platform 100 of FIG. 1A) can be configured to wirelessly communicate with a mobile device (e.g., a smart watch or smart phone—see 102 of FIG. 1A) via a wireless communications link (e.g., Bluetooth LE, Bluetooth, Wi-Fi, and/or Zigbee) established through a communications port (e.g., communications port 117 of FIG. 1B), for example to transmit sensor data collected during use by a user, to the mobile device for signal processing. In addition, or alternatively, the sensing platform can be configured for wired connection (e.g., communications port 117 of FIG. 1B) with a mobile device (e.g., a smart phone) for the transfer of sensor data collected during use by a user (e.g., stored within a memory disposed within the sensor platform).

Sensing System—Data Processing

The processing of raw data/measurements made within the sensor platform can be executed by a processor running on the sensor platform, on a mobile device in communication with the sensor platform (e.g., also functioning as an interface device), and/or on one or more remote servers in communication with the sensor platform and/or the mobile device, to analyze the raw data/measurements (in some embodiments also taking into account contextual information). The sensing system then uses the results to provide advice to users allowing them to adjust their behavior to improve training, competition, and/or recovery results.

Figure 6A:
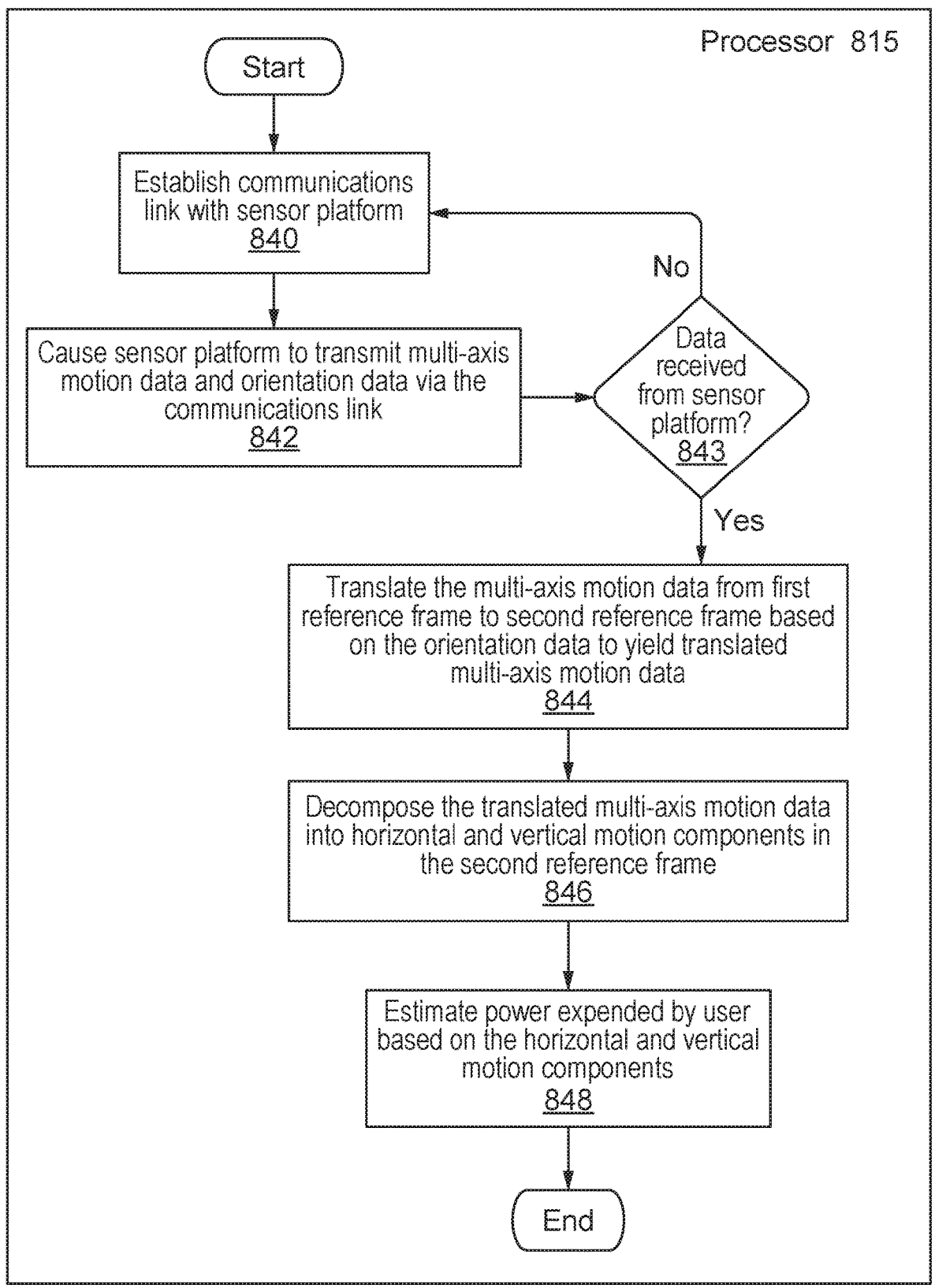
FIG. 6A shows a diagram of the processing of data received by a processor from a sensor platform, according to some embodiments.

An exemplary flowchart, showing the processing of data received from a sensor platform on a processor, is shown in FIG. 6A. A processor 815 (which may be compatible with processor 115 of FIG. 1B, and may reside, for example, in a mobile device) establishes, at 840, a communications link with a sensor platform as described herein (e.g., with reference to FIGS. 1A and 1B). At 842, the processor 815 sends a request to cause the sensor platform to transmit multi-axis motion data and orientation data via the communications link. At 843, if data has not yet been received from the sensor platform (e.g., if the communications link has been interrupted), the processor 815 re-established the communications link at 840. Once the processor 815 has received the multi-axis motion data and orientation data, the processor 815 then translates the multi-axis motion data from a first reference frame (e.g., a fixed reference with respect to the sensor platform) to a second reference frame (e.g., with respect to Earth) based on the orientation data, thereby yielding translated multi-axis motion data. At 846, the processor 815 decomposes the translated multi-axis motion data into horizontal and vertical motion components in the second reference frame. Using the horizontal and vertical motion components determined at 846, the processor 815 then estimates, at 848, the power that has been expended by the user for the period of time in which the multi-axis motion data and orientation data were collected by the sensor platform.

Figure 6B:
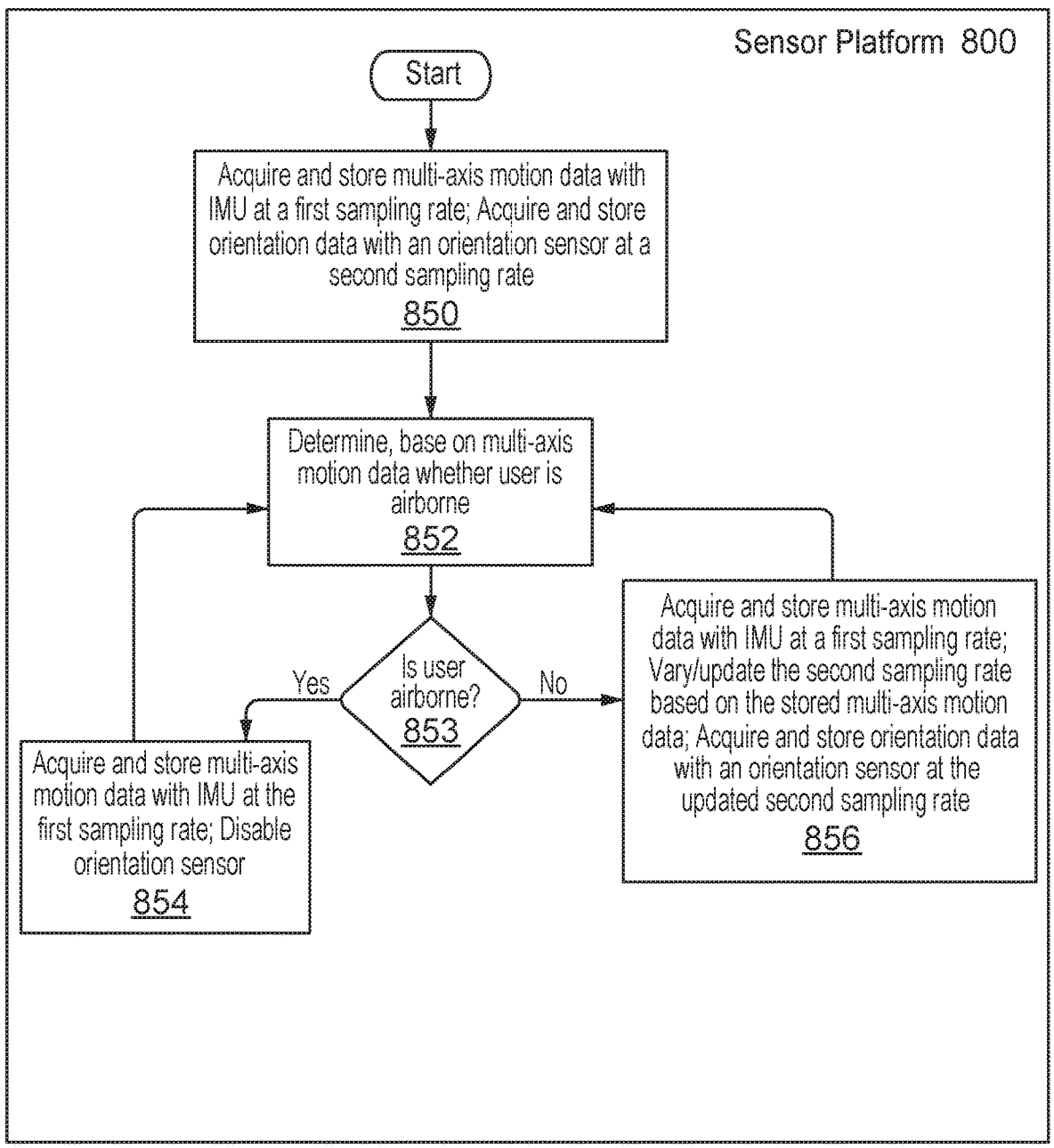
FIG. 6B shows a diagram of the measurement of multi-axis motion and orientation data on a sensor platform, according to some embodiments.

FIG. 6B shows a diagram of the measurement of multi-axis motion and orientation data on a sensor platform, according to some embodiments. At 850, a sensor platform 800 (which may be compatible with the sensor platform 100 of FIG. 1A) acquires, and stores in a memory, multi-axis motion data with an IMU at a first sampling rate, and acquires, and stores in the memory, (e.g., concurrently) orientation data with an orientation sensor at a second sampling rate. The sensor platform determined, at 852, whether the user wearing the sensor platform 800 is airborne (i.e., their feet are not contacting the ground), based on the multi-axis data acquired/stored at 850. If, at 853, the user is airborne, then the sensor platform continues, at 854, to acquire and store multi-axis motion data with the IMU at the first sampling rate, but also disables the orientation sensor. If the user is not airborne at 853, then the sensor platform continues, at 856, to acquire and store multi-axis motion data with the IMU at the first sampling rate, and may vary/update the second sampling rate (of the orientation sensor), e.g., based on the stored multi-axis motion data (which, for example, may be indicative of whether the user is walking, running, etc.). Thus, at 856, the sensor platform 800 also continues to acquire and store orientation data with the orientation sensor, but at the updated second sampling rate. As shown in FIG. 6B, steps 852, 853, 854 and 856 may be iteratively performed, as appropriate, e.g., throughout the duration of time that measurements are taken (e.g., over the course of a run or other bipedal motion of the user).

Figure 7:
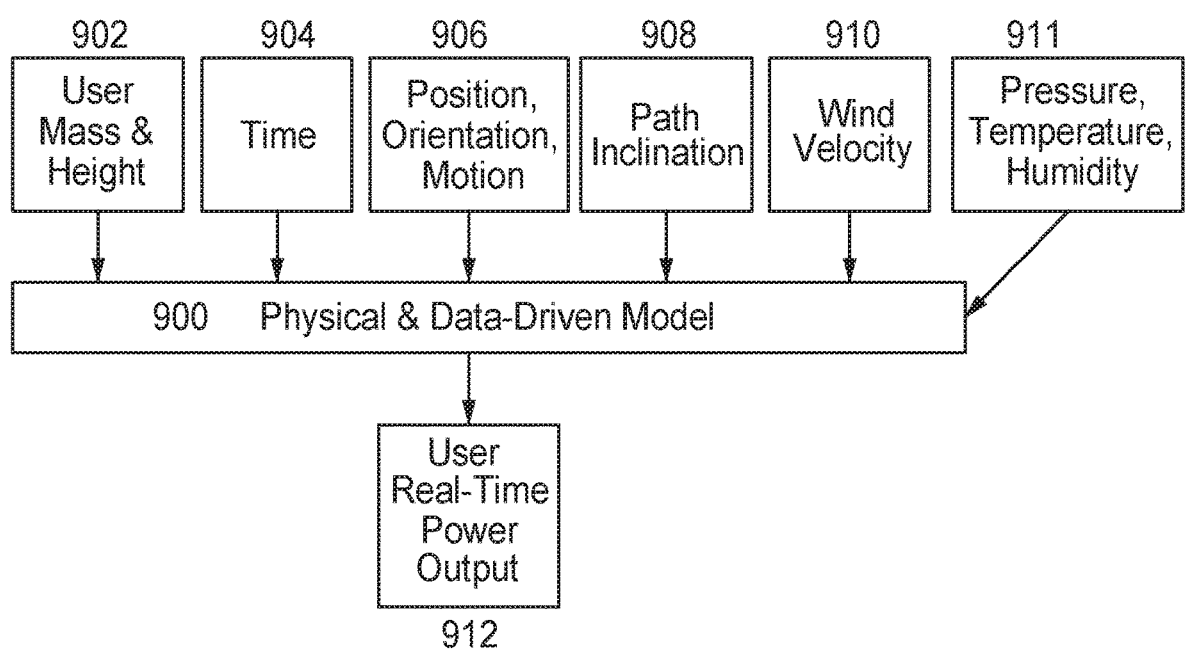
FIG. 7 shows a block diagram of a predictive model, according to some embodiments.

Information derived from sensors and/or from knowledge of constraints on bipedal motion can be supplied to a predictive model (FIG. 7) (e.g., a physical and data-driven model) to estimate accelerations, velocities, positions, and orientations, e.g., based on observed data and/or available knowledge or a subset thereof. For example, as shown in FIG. 7, metrics such as a user's mass and height 902, time 904, position, orientation and motion (906), path inclination 908, and wind velocity 910, are inputs to the predictive model 900, and a user real-time power output 912 is calculated and output.

In some implementations, learned bipedal motion properties for a particular individual are used to increase the accuracy of acceleration, velocity, position, and orientation estimates. These properties may depend on running and/or walking conditions such as incline, fatigue, and pace. Knowledge of running and/or walking conditions can be used to further increase the accuracy of acceleration, velocity, position, and orientation estimates.

The following metrics of interest are calculated based on data gathered from the sensor platform. Their calculation can employ a variety of estimation techniques.

Force Map

The sensor platform may be equipped with one or more location-specific sensors, such as force sensors, flex sensors, and/or temperature sensors, allowing for derivation of a time-varying map of metrics of interest. For example, the device may support measurement of the distribution of impact force across different structures of the feet and legs.

Speed and Distance

Fine-grained limb motion patterns can be used to estimate stride lengths. Timer(s) within the sensing and/or computation devices can be used to determine stride times. These metrics, combined, can be used to calculate the average speed and/or distance traveled of users.

Figure 8:
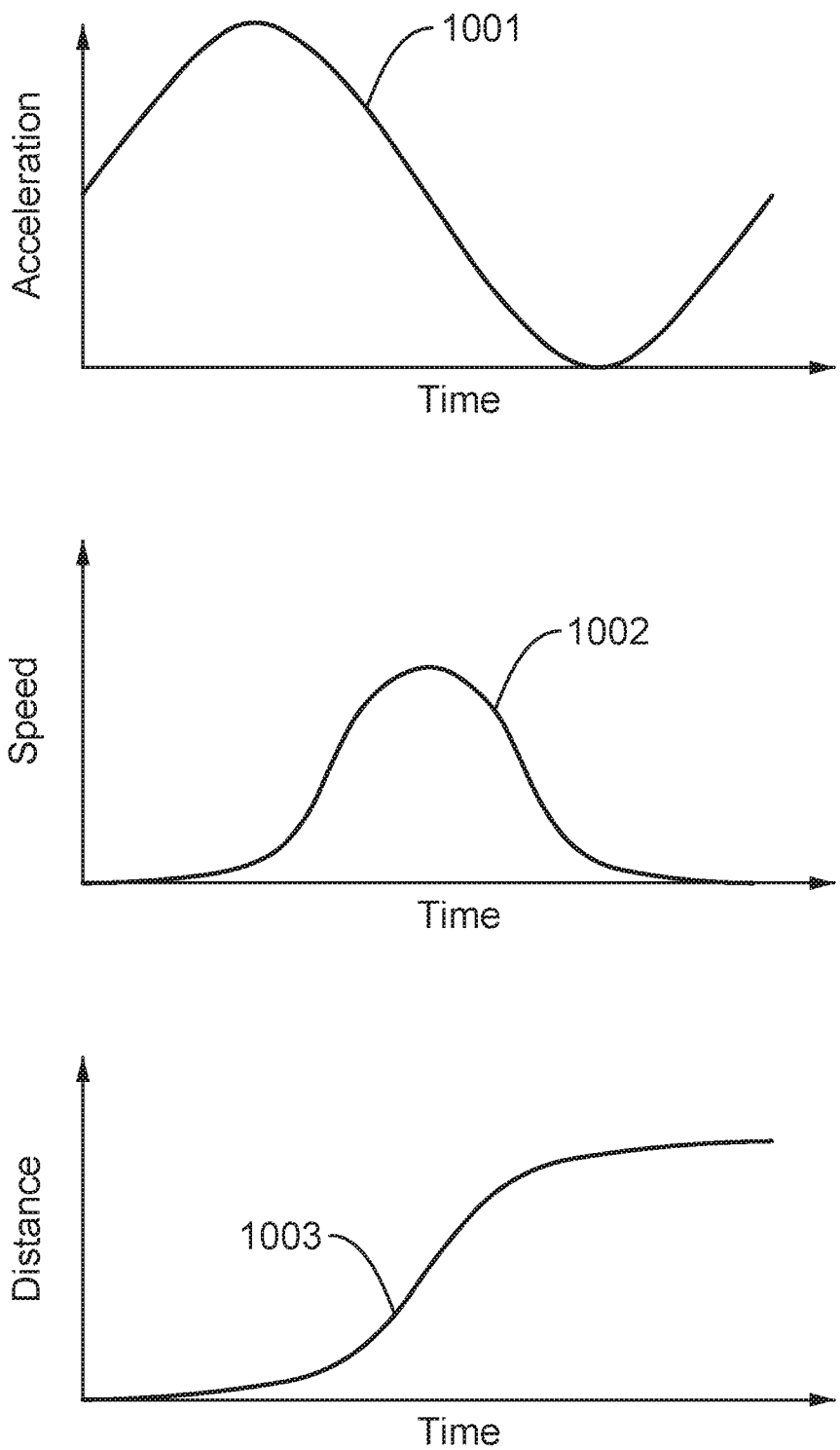
FIG. 8 shows foot acceleration, speed, and distance during bipedal motion, according to some embodiments.

To allow speed and distance to be estimated without frequent use of high energy consumption GPS technologies, data from motion-related sensors calibrated based on context- and person-dependent data can be used. For example, during bipedal motion, foot acceleration can be used to estimate speed and distance. FIG. 8 shows exemplary approximate foot acceleration, speed, and distance for one stride during bipedal motion. In FIG. 8, curve 1001 shows how the foot accelerates with time along the vector pointing in the same direction as the foot, curve 1002 shows how the speed of the foot changes with time along the vector pointing in the same direction as the foot, and curve 1003 shows how the distance of the foot changes with time along the vector pointing in the same direction as the foot. Based on FIG. 8, the distance can be described as follows:

$$\int a e^{-(x-b)^2/c^2} dx = \sqrt{\pi} a |c|$$

where a, b, and c can be derived by using linear regression to fit a Gaussian distribution to a series of sensor samples or via infrequent calibration to GPS data. By using the learned parameters for a particular individual, and possibly activity, the speed and distance estimation accuracy possible with low-power acceleration sensors is improved.

The accuracy of the speed and distance estimation technique described in the above paragraph can be further improved by infrequent calibration using GPS technology. For example, distance estimation error that may accumulate over long estimation periods can be corrected via very infrequent GPS measurements, thus allowing accuracy typical of GPS with energy consumption typical of acceleration sensors. These infrequent GPS readings can also be used to calculate new calibration parameters for the equations described in the previous paragraph, further improving accuracy even in the absence of future GPS measurements.

Direction

Accelerometers, gyroscopes, and compasses can be used to estimate changes in direction of motion. Contextual information, such as knowledge of motion patterns possible for a particular activity or paths possible from a particular location, can be used to constrain direction estimates, thereby correcting for sensing noise.

Displacement

Techniques described herein, that enable tracking the motion and orientations of body parts over time, may also be used to estimate the coarse-grained location and/or velocity of a person. They may also be used to track the paths and orientations of limbs during athletic activities such as running, or swinging a baseball. Orientation-corrected accelerometer readings can be integrated over time to determine a three-dimensional path of the limbs being monitored by sensing platforms.

In some embodiments, variation in pressure across multiple barometric pressure sensors and time is used to estimate speed and changes in speed.

Incline

Improved estimates of valuable information can be obtained if the incline of the surface on which the user is moving is known. To determine current incline, the instantaneous derivative of altitude can be approximated by combining timed barometric pressure samples and pace data to allow fitting of a linear incline function, for example to determine instantaneous incline, thereby making long-term variation in barometric pressure due to changes in weather irrelevant. Alternatively or in addition, incline can be estimated using the position and direction estimation techniques described herein and a map stored on the sensing system translating from position and direction to incline. Incline can also be determined by pressure measurements (using a pressure sensor, such as a barometer, pressure altimeter, and/or the like). For example, a pressure sensor can be used to detect changes in a user's elevation (i.e., attitude or vertical position). Low-pass filtering (e.g., with a cutoff frequency of ~0.2 Hz) of the pressure sensor signal can also be used to compensate for air that is incident on the runner (e.g., strong winds, abrupt changes in wind patterns, and/or other aerodynamic factors). The cutoff frequency can be changed dynamically to account for changes in a runner's attitude.

Body Forces

One or more of the following data elements can be used to estimate the forces acting on particular body parts, including the center of mass: acceleration data in body or Earth frame of reference, incline, user weight or mass, and user height. Mass and height may be used to estimate the distribution of body mass across different parts of the body.

Force can be calculated using knowledge of change in kinetic energy over time, m×a, where m is mass and a is the acceleration. In one embodiment, force acting on a runner's center of mass is estimated using the acceleration at the sensing platform location. By knowing the weight and height of the person, a scaling factor can be used to scale the acceleration seen at a sensor location, such as the hip or trunk, to the acceleration of the center of mass across a wide range of running speeds and cadences. A general scaling factor may be used for all users, or a user-specific scaling factor may be used if more information about the user's body structure is known. These approaches can be used to estimate both vertical and horizontal forces.

The inventors have determined, through laboratory testing, that when running downhill, only a portion of potential energy is recovered and can be used to permit reduced muscle power for the same overall force acting on the body center of mass. Therefore, a potential energy recovery efficiency scaling factor can be used to determine the impact of up-hill or down-hill running on body output power. In other embodiments, instead of using a scaling factor, the velocity of the body part of interest is again integrated to determine the position and the following expression is used to estimate the power required for vertical motion:

$$\frac{kmg\Delta h}{\Delta t}$$

where k is a scaling factor, m is the mass, g is the acceleration due to gravity, $\Delta h$ is the change in sensor height, and $\Delta t$ is the change in time.

Air Resistance and Wind Effect

Air resistance and wind may affect human velocity and required force exertion, and hence the mechanical power output. What is needed is a method of determining the power being applied to a human body by its own muscles in the presence of air resistance and/or in the presence of moving air or wind.

Figure 9:
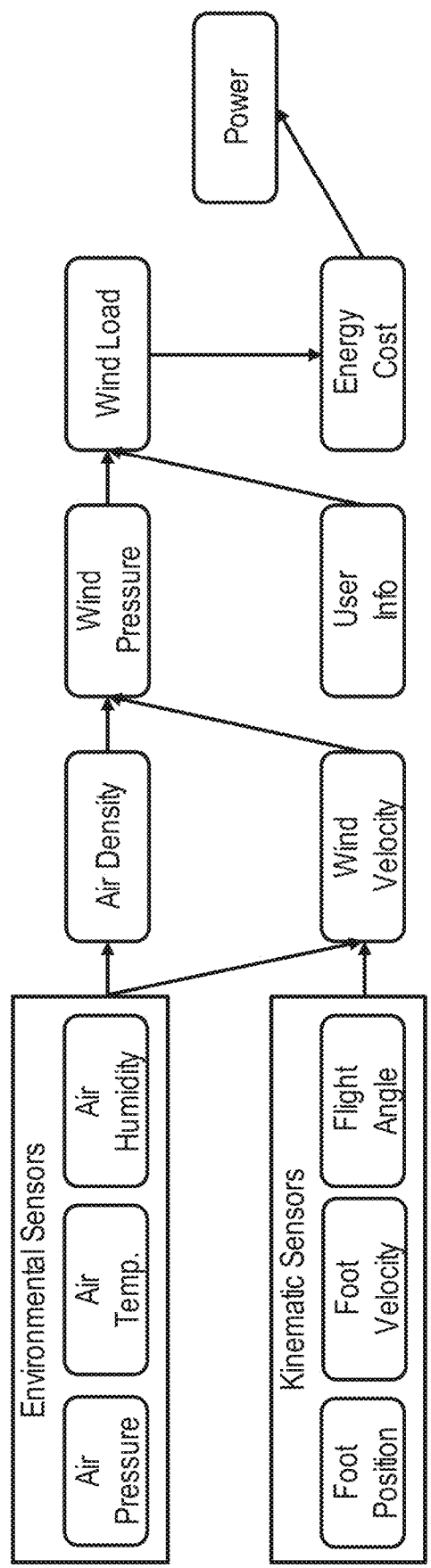
FIG. 9 shows an overview of the integration of environmental sensed data, kinematic sensed data, and user information to calculate air density, wind velocity, wind pressure, wind load, and the power required to overcome wind.

Towards that end, the sensing platform described herein measure real-time barometric pressure sensed from anterior and/or posterior facing, and/or side facing, surface and/or surfaces of a body in motion, such as a person who is running, walking, or otherwise in motion. The sensing platform may measure the ambient temperature of the air mass surrounding a body in motion. The sensing platform may measure the ambient relative humidity of the air mass surrounding a body in motion. The sensing platform may determine the current global positioning of a body in motion. The sensing platform may determine the real-time instantaneous velocity of a body in motion. The sensing platform may determine a real-time instantaneous position, velocity, and orientation of one or more sensors, or nodes, of a sensor attachment point on the body of in motion, (e.g., a foot). For example, as shown in FIG. 9, a sensor node (or module) can include kinematic sensors (e.g., an IMU and/or gyroscopes) operable to determine a position, velocity, and/or angle of a foot. Additionally, the sensor node can include environmental sensors, such as a pressure sensor, a temperature sensor, and a humidity sensor.

A single pressure sensor may sample pressure, and an inertial measuring unit may measure position and orientation, at multiple times during a single footstep of a body in motion in order in order to capture pressure, position, and orientation profiles of the body in motion at a sufficiently high frequency to capture pressure, position, and orientation variations during the course of each step. Each measured pressure may be correlated to a position and orientation measurement from the plurality of position and orientation measurements by acquiring the pressure, position, and orientation measurements at the same time and at the same location. The pressures, positions, and orientations will vary as a runner's foot strikes the ground, pushes off, and is airborne between steps. Air pressure due to wind may be most accurately measured when the runner's foot is pointed into the wind, while in midair. Therefore, measured pressures may vary during the course of a single step due to the position and orientation of the sensor on, for example, a node affixed to a runner's shoe. By measuring pressure, position, and orientation multiple times during each footstep, it is possible to calculate pressure statistics, including a maximum pressure that may correspond to a dynamic pressure due to air resistance from wind, and an underlying static pressure corresponding to a minimum air pressure measured through several strides. In general, the static air pressure varies at a lower frequency than the dynamic pressure due to air pressure including wind as a runner's foot changes position and orientation with respect to wind. Therefore, a single pressure sensor may be used to calculate or estimate both a static pressure and a dynamic pressure (kick pressure), in a method that's analogous to the operation of a pitot tube on an aircraft that measures airspeed based on the difference between static pressure that varies based on elevation, and dynamic pressure from air speed and wind.

As noted above, the sensing system may contain one or more pressure sensors that may be placed at one or more locations around the human body. By way of example, locations may include within or on a strap or clip attached to the foot, ankle, leg, wrist, torso, or head. Each location has one or more of the following advantages: (a) convenience to the user and (b) accuracy of measuring air resistance amplitude and direction.

The sensing system may measure air pressure at one or more anterior, side, or posterior locations of the body. In some embodiments, accuracy can be increased by measuring the air pressure at both the anterior and posterior of the body.

The sensing system may contain one or multiple temperature sensors. As shown in FIG. 9, temperature and/or humidity compensation may be applied to determine an air density, which can be used to correct wind velocity and/or wind pressure calculations. Then the air pressure difference, $P_{diff}$, between the anterior and posterior of the body, can be computed by subtracting the corresponding air pressure readings (with and/or without temperature compensation). Filtering may be applied (e.g., a low-pass filter with a cutoff frequency of 0.1 Hz, 0.2 Hz, or some other frequency). Alternatively, a band-pass filter with a frequency range of 0.1-0.3 Hz or some other frequency range may be used.

For some embodiments, the IMU may report the real-time linear and angular acceleration. Using a method described herein, the linear acceleration along the physical dimension may be determined. When the body in motion is moving, the forward acceleration a can be determined during the air time, i.e., when the body has completely left the ground. Then, the wind-induced force can be determined as m×a, where m is the body mass. Next, the wind-induced power can be determined by v×f, where v is the body velocity along the forward direction.

The pressure sensor(s) (e.g., barometric sensor(s)) can also be used to determine the wind-induced power or energy cost associated with wind. In some embodiments, the air pressures at the anterior and posterior of the user's body are measured by the sensing platform, and the difference between these two, i.e., wind pressure P, is computed. Then the wind-induced force (or Wind Load) can be determined by A×P×C, where A is the body forward-facing surface area, and C is the drag coefficient. Similarly stated, as shown in FIG. 9, information about the user (e.g., surface area and or drag coefficient) and wind pressure can be used to calculate a wind load.

The air resistance and wind effect can also be estimated as follows. First, human body velocity information is estimated using inertial sensors and/or GPS sensors. The wind velocity is determined using an in-situ wind sensor or third-party weather information. Then, the relative velocity, v, between the human body and wind can be determined. Next, the wind pressure can be determined by K×$v^2$, where K is a coefficient.

Barometric pressure samples may be acquired by one or more sensors at a frequency that may be fixed or adjusted based on the computed expected accuracy of the current air resistance and current system requirements. These data represent the barometric pressure at a particular sensor location, which can be translated into the overall air pressure a runner is experiencing across their body.

In the case of placing the a sensing system node on a limb (e.g., foot, ankle, leg, wrist, upper arm, forearm, etc.) kinematic data from an accelerometer and/or gyroscope can be combined with barometric pressure data for a more accurate result due to the pressure ($P_{air}$) increasing quadratically with velocity v.

$$P_{air}=0.5*p*C_d*v^2$$

Knowing the velocity of the limb (e.g., based on kinematic data) can account for the pressure increases due to the individual limb movement. At the same time the additional velocity from the limb swing serves to amplify the barometric pressure measurement and thereby increase the signal-to-noise ratios of the measurement, due to the nonlinear relationship of air speed relative to limb speed and the air pressure resulting therefrom.

Multiple sensors can also be used to improve the improve wind speed magnitude accuracy and/or to determine a more accurate wind heading relative to the direction of over earth body movement. On the torso and/or limbs, a network of barometric pressure sensors spread around the front, back, and/or sides of the body, with the component count and component body placement location selection driven by application requirements, e.g., accuracy requirements, system power requirements, and/or ease of use requirements. Such a multi-component network can be used to determine pressure gradients has formed across the sensor network, and across the body, thus allowing the direction and intensity of wind to be calculated. For more precise wind direction and speed information, more sensors can be used at more diverse sets of body location placements.

One or more of the following data elements are used to estimate the forces, from the air pressure, acting on particular body parts, including the center of mass: acceleration data in body with respect to gravity, or Earth frame of reference, gyroscopic data and device orientation information, barometric pressure, temperature, humidity, user weight or mass, and user height. Mass and height may be used to estimate the drag coefficient and cross sectional area ($C_d*A$) to a sufficiently high degree of accuracy for the runner, walker, hiker, or person engaging in any other suitable activity. Pressure, temperature and humidity can be used to estimate air density (p). The Sensing system's accelerometer and gyroscope data can be combined with high frequency barometric pressure readings to estimate the air speed relative to the runner(v). Finally force imparted from the air mass on the human body can be calculated using the following equation:

$$F_{air}=0.5*p*C_d*A*v^2,$$

where p is the air density, $C_d$ is the drag coefficient, A is the cross sectional area, and v is the velocity of the air relative to the runner. These values may be measured, calculated, or otherwise estimated using any suitable technique. For one example, $C_d$ can be calculated using techniques such as those described in Pugh, L. G. C. E. "The Influence of Wind Resistance in Running and Walking and the Mechanical Efficiency of Work Against Horizontal or Vertical Forces, 213 J. Physiol. (1971), 213, pp. 255-276, the disclosure of which is hereby incorporated by reference in its entirety.

The velocities of parts of the user's body can be determined using data from accelerometers, magnetic sensors, and/or gyroscopic sensors. In some embodiments, force acting on a runner's center of mass can be estimated using the velocity at the Sensing Platform location. By knowing the weight and height of the person, a scaling factor can be used to scale the velocity of the person as measured at a sensor location, such as the hip or trunk, to the velocity of the center of mass across a wide range of running speeds and cadences. In the absence of scaling factors calibrated to the user, a general scaling factor may be used which suitably works for all users, or a user-specific scaling factor may be used if more information about the user's body structure is known or calibrated for. This approach can be used to estimate both vertical and horizontal forces imparted on the body by air masses.

Air pressure or wind force can vary within a stride because it is a superlinear function of air speed relative to the body. In order to accurately account for such changes in relative air speed, the wind force can be used to calculate mass-normalized air speed, which can then be used to recalculate wind force at different relative air speeds resulting from changing body speed during the stride.

Next, the impact of the wind effect on the power required to walk or run can be computed by the sensor platform as follows. Walking or running power ($P_{walk}/P_{run}$) introduced by wind effect equals wind force multiplied by walking or running speed, which in turn equals the anterior-posterior air pressure difference ($P_{diff}$) multiplied by the equivalent anterior surface area of the human body ($A_{anterior}$) multiplied by the walking or running speed (v), i.e., $$\text{power}=P_{diff}*A_{anterior}*v,$$

where $A_{anterior}$ is determined by taking the surface integral of the dot product of a unit vector pointing from the posterior to the anterior of the body with the unit vector normal to the surface of the body at each point on the surface where the dot product is positive.

Known methods for exercise training, such as monitoring heart rate, pace, or cadence generally fail to account for effort to overcome wind/air resistance and therefore can become measuring power and accounting for power expended to overcome air/wind resistance can provide a more accurate training guidance, particularly in the presence of strong wind. Similarly stated, embodiments described herein can be operable to provide accurate guidance regarding training exertion in the presence of wind, which can allow the user to achieve specific adaptations, such as improved speed or performance, unlike known methods, which may instruct users to engage in above-target exertion in the presence of a head wind and/or below-target exertion in the presence of a tail wind.

In some embodiments, walking or running speed estimation can be combined with take-off and landing acceleration to determine the impact of wind on running power. Patent application PCT/US2015/051181 describes methods of measuring and/or estimating walking/running speed (v), air time ($t_{air}$), and the take-off velocity ($v_{take-off}$). Multiplying the walking/running speed by air time yields the distance traversed by the body during the air time ($D_{air}$):

$$D_{air} = v * t_{air}$$

By taking the dot product of the unit vector pointing from the posterior to the anterior of the body with the take-off velocity, the forward take-off velocity ($v_{forward}$) can be determined. By multiplying by the air time ($t_{air}$), the distance that would be covered during the air time in the absence of wind ($D_{ideal}$) can be determined:

$$D_{ideal} = v_{forward} * t_{air}.$$

If $D_{air}$ is unequal to $D_{ideal}$, the power required for running at a particular speed is being influenced by wind, or air resistance. This can be used to test for the influence of wind. The Wind Force ($F_{wind}$) can be Determined as Follows:

$$F_{wind} = M_{body} * \left( \frac{2 * D_{air}}{t_{air}^2} - \frac{2 * v_{forward}}{t_{air}} \right),$$

where $M_{body}$ is the body's mass, $D_{air}$ is the forward distance traveled during air time, $v_{forward}$ is the forward speed, and $t_{air}$ is the air time duration. The wind force can be used to determine instantaneous wind power by multiplying by instantaneous body velocity. In some embodiments, the system accounts for changes to wind power during a stride by considering the impact of changing instantaneous forward speed on wind power.

Impact

Temporal changes and patterns in the acceleration experienced by the sensing device can be used to determine the time of impact, after which samples in a short time window can be used to estimate impact forces along multiple physical axes.

Ground Time and Air Time

Full frequency spectrum motion metrics can be analyzed to determine when a user's limb is in contact with the ground, allowing calculation of ground time and air time. These metrics can be used to guide users toward improvement in athletic form.

Power Number

One embodiment of the present disclosure determines the power being exerted by a human body's muscles on itself using dynamically changing data gathered using a compact body-mounted wireless sensing platform containing one or more of the following sensor types: three-axis accelerometers, gyroscopes, magnetometers, Global Positioning System (GPS) receivers, and atmospheric or air pressure sensors. This power measurement may be used to assist athletic training.

The sensing system can incorporate implementations of signal processing techniques that take into account known physical properties of human running and/or walking behavior to determine forces (e.g., including wind-related forces) and/or velocities. Combined with an in-system timer, the force and velocity information permit the calculation of body power consumption (e.g., a "power number"). The power number can also be derived, at least in part, from acceleration measurements (e.g., collected by the IMU of the sensor platform).

This power number can be used, e.g., in combination with pace and/or duration, to guide the user toward more appropriate training, pace, and running and/or walking technique. For example, power can be used to enable users to understand the relationship between body power output during running and/or walking and the durations particular power outputs can be maintained. This relationship can be used to quantify the strengths and weaknesses of users, and suggest changes in training plans. Body power output can also be used during runs to recommend appropriate instantaneous paces to users in order to increase or maximize entire-run pace in the presence of varying fatigue and running and/or walking environment. Power is also used to determine which changes in running and/or walking form or technique improve or degrade running and/or walking efficiency. Running and/or walking efficiency at a particular speed is inversely related to running and/or walking power.

A method of estimating power expended by a user while wearing a sensor platform containing an inertial measurement unit (IMU) and a memory can include storing, in the memory, (i) multi-axis motion data and (ii) orientation data, where the multi-axis motion data represents motion measured by the IMU in a first reference frame fixed with respect to the sensor platform, and the orientation measurements represent orientation of the sensor platform in a second reference frame fixed with respect to the Earth. A communications link is established between a processor (e.g., of a mobile device) and the sensor platform. The sensor platform is caused to transmit the multi-axis motion data and the orientation data to the processor via the communications link. The processor translates the multi-axis motion data from the first reference frame to the second reference frame based on the orientation data so as to yield translated multi-axis motion data. The processor decomposes the translated multi-axis motion data into horizontal motion components and vertical motion components in the second reference frame. In some embodiments, the processor decomposes the translated multi-axis motion data into transverse motion components and vertical components, for which the transverse motion components are parallel to a ground plane. The processor then estimates the power expended by the user based on the horizontal motion components and the vertical motion components (for example, vertical power expended may be estimated based on the vertical motion components and horizontal power expended may be estimated based on the horizontal motion component).

Vertical Power can be Estimated as Follows:

$$Power_{vertical} = \frac{k1 \times m \times g \times \Delta h}{\Delta t}$$

where k1 is a scaling factor, m is the mass, g is the acceleration due to gravity, Δh is the change in height, and Δt is the change in time. Δh can be understood to be an "incline of a path" of the user (e.g., a runner), and can be determined by pressure sensor readings (e.g., barometer 101 of FIG. 1B, or by any other atmospheric or air pressure sensor), vertical motion data acquired from the IMU (e.g., a three-axis accelerometer), and/or GPS-derived position data. In some implementations, to save on battery power consumption, GPS position data is not acquired, or is only infrequently acquired (e.g., to recalibrate measurements, etc.).

Horizontal Power can be Estimated as Follows:

$$Power_{horizontal} = k2 \times F \times V = k2 \times m \times a \times V$$

where k2 is a scaling factor, F is the force, m is the mass, a is the acceleration, and V is the speed.

In Addition, or Alternatively, Horizontal Power can be Estimated as Follows:

$$Power_{horizontal} = \frac{k3 \times m \times V \times \Delta V}{\Delta t} \approx \frac{k4}{\Delta t} \times (k5 + k6 \times \Delta V) \times \Delta V$$

where k3, k4, k5, k6 are scaling factors, m is the mass, α is the acceleration, and ΔV is the change of speed during the period of Δt.

The scaling factors (k1, k2, k3, k4, k5, k6) may be empirically determined based on measurement of one or multiple users (e.g., averaged across a group of runners and thus broadly applicable) and/or determined based on information provided by the specific user (e.g., the scaling factors can be "constants" that are computed for an individual user based on measured, tested, historical, and/or known parameters/values). "Known" parameters/values can refer to parameters/values that have been manually entered into the sensing system (e.g., via a user interface) by the user or a trainer. Each of the scaling factors (k1, k2, k3, k4, k5, k6) can be human-specific, user-specific (e.g., based on their level of general physical fitness, sport-specific fitness, running form, height and/or weight, muscle conditioning, genetics, etc.), body part specific, and/or specific to a given environment, terrain, elevation, types of apparel or footwear that a user is wearing, etc. In some implementations, one or more of the scaling factors or constants may be initialized to have generalized values (e.g., based on studies of a large group of individuals) and, over time, as the sensing system has gathered, stored, and/or processed sensor data for a specific user, the scaling factors or constants may vary to become more customized, either automatically or by manual request of a user.

In some cases, one or both of the above estimates of power expended by the user accounts for the wind resistance (e.g., based on pressure sensor data), e.g., via one or more of scaling factors (k1, k2, k3, k4, k5, k6).

Estimating the power expended by the user can include estimating power expended for vertical motion of the user. Alternatively or in addition, estimating the power expended by the user can include scaling, via a scaling factor, an acceleration of the user to the user's center of mass, for example, wherein the scaling factor is based on a height of the user and a weight of the user.

The method can include estimating a metabolic energy expenditure (i.e., calories burned) of the user based on the power expended by the user. The metabolic energy expenditure can be estimated as follows:

$$Energy_{metabolic} = \int_{T1}^{T2} \frac{Power(t) \times (1 - k7(t))}{l(t)} dt$$

where Power(t) is the power output at time t, k7(t) is a coefficient which measures the contribution of recycled power during human running, l(t) is the running economy coefficient, which measures the percentage of the metabolic energy transformed into mechanical power output. T1 and T2 define the period of time of interest.

The Metabolic Energy Expenditure can Also be Estimated as Follows:

$$Energy_{metabolic} = \int_{T1}^{T2} Power(t) \times Constant(t) dt$$

where Power(t) is the power output at time t, T1 and T2 define the period of time of interest, and Constant(t) is an empirically-determined and/or customized constant value based on or derived from one or more of the following: (1) k7(t) (the coefficient which measures the contribution of recycled power during human running); (2) l(t) (the running economy coefficient, which measures the percentage of the metabolic energy transformed into mechanical power output); (3) measured or known lactate threshold or anaerobic threshold of the user; (4) measured, historical or known $VO_2$ max (maximal oxygen consumption) of the user; (5) measured, historical or known running economy of the user; (6) measured, historical or known performance-impacting physiological parameters of the user; and (7) measured, historical or known performance-impacting physiological parameters of a "typical" or "average" runner (e.g., as determined by averaging across a general pool of runners, or as determined by averaging across a pool of runners that matching a specified profile of the specific user). "Known" values can refer to values that have been manually entered into the sensing system (e.g., via a user interface) by the user or a trainer.

The sensor platform can include a pressure sensor, and the method in such instances can include: (1) causing the sensor platform to transmit pressure data to the processor via the communications link, the pressure data representing pressure measurements by the pressure sensor; and (2) estimating, by the processor, wind resistance experienced by the user based on the pressure data. Estimating the power expended by the user can include accounting for the wind resistance. In other instances where the sensor platform includes a pressure sensor, the method can include: (1) causing the sensor platform to transmit pressure data to the processor via the communications link, the pressure data representing pressure measurements by the pressure sensor; and (2) estimating, by the processor, an incline of a path of the user based on the pressure measurements and the translated multi-axis motion data.

The method can include estimating (e.g., via a processor running on the sensor platform and/or on a mobile device in wireless or wired communication with the sensor platform) one or more of a plurality of metrics of interest. For example, a stride distance of the user can be estimated based on the multi-axis motion data and/or the translated multi-axis motion data as described herein. An amount of time during a stride of the user that a foot of the user is airborne can be estimated based on the multi-axis motion data and/or the translated multi-axis motion data. An efficiency of the user can be estimated based on the power expended by the user and an amount of time during the stride of the user that the foot of the user is airborne. An amount of time during the stride of the user that the foot of the user is in contact with the ground can be estimated based on the multi-axis motion data and/or the translated multi-axis motion data. A fatigue of the user can be estimated based on the amount of time during the stride of the user that the foot of the user is airborne and the amount of time during the stride of the user that the foot of the user is in contact with the ground. A form consistency of the user can be estimated based on the amount of time during the stride of the user that the foot of the user is airborne and/or the amount of time during the stride of the user that the foot of the user is in contact with the ground. A performance of the user can be estimated based on the amount of time during the stride of the user that the foot of the user is airborne and/or the amount of time during the stride of the user that the foot of the user is in contact with the ground. For a given implementation, a sensor platform may be configured to estimate any combination of the foregoing metrics of interest.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments of technology disclosed herein may be implemented using hardware, software, or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes (e.g., of designing and making the technology disclosed above) outlined herein may be coded as software that is executable on one or more processors that employ any one of a variety of operating systems or platforms. Additionally, such software may be written using any of a number of suitable programming languages and/or programming or scripting tools, and may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the disclosure discussed above. The computer readable medium or media can be transportable, such that the program or programs stored thereon can be loaded onto one or more different computers or other processors to implement various aspects of the present disclosure as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present disclosure need not reside on a single computer or processor but may be distributed in a modular fashion amongst a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method, comprising:
   measuring, using an inertial measurement unit (IMU) a plurality of positions of a foot of an animal body while the foot is in motion, the IMU disposed within a sensor housing coupled to the foot of the animal body;
   measuring a plurality of measured pressures using a pressure sensor disposed within a pressure chamber defined by the sensor housing, the pressure chamber having an opening enabling communication of pressure from at least one of an anterior side or a posterior side of the animal body such the plurality of measured pressures are pressures experienced by at least one of an anterior portion of the foot or a posterior portion of the foot while the foot is in motion;
   correlating, each measured pressure from the plurality of measured pressures to a position from the plurality of positions;
   calculating, by a processor, a static pressure based on the plurality of measured pressures and positions correlated to the plurality of measured pressures;
   calculating, by the processor, a maximum pressure of the plurality of measured pressures; and
   calculating an air-induced power exerted on an entirety of the animal body based on the static pressure and the maximum pressure.

2. The method of claim 1, further comprising:
   calculating, by the processor, a velocity of the foot of the animal body based on the plurality of positions of the foot of the animal body;
   calculating, by the processor, a dynamic pressure, the dynamic pressure equal to a difference between the maximum pressure and the static pressure; and
   calculating, by the processor, an air velocity based on the velocity of the foot of the animal body, a square root of the dynamic pressure, and an air density.

3. The method of claim 2, further comprising:
   calculating, by the processor, an air-induced force exerted on the entirety of the animal body based on the air velocity, the air density, a drag coefficient of the animal body, and an anterior surface area of the animal body; and calculating, by the processor, the air-induced power exerted by the animal to overcome the air-induced force based on the air-induced force and a velocity of the entirety of the animal body.

4. The method of claim 1, wherein the air-induced power is calculated based on an air density, the method further comprising:

compensating, by the processor, the air density based on a temperature.

5. The method of claim 1, wherein the air-induced power is calculated based on an air density, the method further comprising:

compensating, by the processor, the air density based on a humidity level.

6. The method of claim 1, further comprising:

measuring, by the IMU, multi-axis motion data and orientation data for the animal body, the multi-axis motion data representing motion measured by the IMU in a first reference frame fixed with respect to the sensor housing and the orientation data representing an orientation of the sensor housing in a second reference frame fixed with respect to gravity;

translating, by the processor, the multi-axis motion data from the first reference frame to the second reference frame based on the orientation data to yield translated multi-axis motion data;

decomposing, by the processor, the translated multi-axis motion data into horizontal motion components and vertical motion components in the second reference frame; and calculating, by the processor, power expended by the animal body based on the horizontal motion components, the vertical motion components, and the air induced power.

7. The method of claim 1, further comprising:

measuring, by the IMU, multi-axis motion data and orientation data for the animal body, the multi-axis motion data representing motion measured by the IMU in a first reference frame fixed with respect to the sensor housing and the orientation data representing an orientation of the sensor housing in a second reference frame fixed with respect to a direction of gravity;

translating, by the processor, the multi-axis motion data from the first reference frame to the second reference frame based on the orientation data to yield translated multi-axis motion data;

decomposing, by the processor, the translated multi-axis motion data into transverse motion components and vertical motion components in the second reference frame, the transverse motion components parallel to a ground plane; and calculating, by the processor, power expended by the animal body based on the transverse motion components, the vertical motion components, and the air induced power.

8. The method of claim 1, further comprising measuring a temperature and/or a humidity level, wherein the processor is further configured to calculate an air density based on the temperature and/or the humidity level, and the plurality of measured pressures.

9. The method of claim 1, further comprising:

calculating, by the processor, a drag coefficient and a cross sectional area of the animal body based on a height and/or a weight of the animal body.

10. The method of claim 1, further comprising:

measuring, by the IMU, multi-axis motion data and orientation data of the foot, the multi-axis motion data representing motion measured by the IMU in a first reference frame fixed with respect to the sensor and the orientation data representing an orientation of the sensor in a second reference frame fixed with respect to a direction of gravity;

translating, by the processor, the multi-axis motion data from the first reference frame to the second reference frame based on the orientation data to yield translated multi-axis motion data; and calculating an incline of a path of the entirety of the animal body based on multi-axis motion data, and/or the plurality of measured pressures.

11. The method of claim 1, further comprising:

calculating a metabolic energy expenditure of the animal based on the air-induced power.

12. The method of claim 1, wherein the sensor is attached to an anterior portion of the foot.

13. A method, comprising:

measuring, using an inertial measurement unit (IMU), kinematic data of a foot of an animal body while the foot is in motion, the IMU disposed within a sensor housing coupled to the foot;

measuring, using a pressure sensor disposed within a pressure chamber defined by the sensor housing, a plurality of measured pressures using a pressure sensor disposed within a pressure chamber defined by the sensor housing, the pressure chamber having an opening enabling communication of pressure from at least one of an anterior side or a posterior side of the animal body such the plurality of measured pressures are pressures experienced by at least one of an anterior portion of the foot or a posterior portion of the foot while the foot is in motion;

correlating, each measured pressure from the plurality of measured pressures to the kinematic data;

calculating, by a processor, a static pressure based on the plurality of measured pressures and the correlated kinematic data;

calculating, by the processor, a dynamic pressure from the plurality of measured pressures; and calculating an air-induced power exerted on the animal body based on the static pressure and the dynamic pressure.

14. The method of claim 13, wherein the dynamic pressure is a kick pressure.

15. The method of claim 13, further comprising:

measuring, by the sensor, a temperature; and compensating, by the processor, the air density based on the temperature.

16. The method of claim 13, further comprising:

measuring, by the sensor, a humidity level; and compensating, by the processor, the air density based on the humidity level.

17. The method of claim 13, further comprising:

measuring, by the IMU, multi-axis motion data and orientation data for the foot, the multi-axis motion data representing motion measured by the IMU in a first reference frame fixed with respect to the sensor and the orientation data representing an orientation of the sensor in a second reference frame fixed with respect to gravity;

translating, by the processor, the multi-axis motion data from the first reference frame to the second reference frame based on the orientation data to yield translated multi-axis motion data;

decomposing, by the processor, the translated multi-axis motion data into horizontal motion components and vertical motion components in the second reference frame; and calculating, by the processor, power expended by the animal body based on the horizontal motion components, the vertical motion components, and the air induced power.

18. The method of claim 13, further comprising:

measuring, by the IMU, multi-axis motion data and orientation data for the foot, the multi-axis motion data representing motion measured by the IMU in a first reference frame fixed with respect to the sensor and the orientation data representing an orientation of the sensor in a second reference frame fixed with respect to a direction of gravity;

translating, by the processor, the multi-axis motion data from the first reference frame to the second reference frame based on the orientation data to yield translated multi-axis motion data;

decomposing, by the processor, the translated multi-axis motion data into transverse motion components and vertical motion components in the second reference frame, the transverse motion components parallel to a ground plane; and calculating, by the processor, power expended by the animal body based on the transverse motion components, the vertical motion components, and the air induced power.

19. The method of claim 13, wherein the sensor is attached to an anterior portion of the foot.

20. An apparatus, comprising:

a housing configured to be attached to a foot of an animal body;

an inertial measurement unit (IMU) disposed within the housing and configured to measure multi-axis motion data associated with the foot of the animal body;

a pressure sensor disposed within a pressure chamber defined by the housing, the pressure chamber having an opening enabling communication of pressure from at least one of an anterior side or a posterior side of the animal body;

a processor; and a non-transitory processor-readable memory storing code configured to be executed by the processor to cause the processor to:

receive signals indicating a plurality of pressures measured by the pressure sensor and indicating pressures experienced by at least one of an anterior portion of the foot or a posterior portion of the foot while the housing is coupled to the foot;

correlate, each measured pressure from the plurality of measured pressures to a position of the foot based on data received from the IMU;

calculate a static pressure based on the plurality of measured pressures and the correlated positions of the foot; and calculate at least one of a maximum pressure or a dynamic pressure from the plurality of measured pressures; and calculate an air-induced power exerted on the animal body based on the static pressure and the at least one of the dynamic pressure or the maximum pressure.

21. The apparatus of claim 20, further comprising:

a clip portion of the housing, the clip portion of the housing defining the opening, the opening aligned with the pressure chamber of the housing.

22. The apparatus of claim 20, wherein the multi-axis motion data measured by the IMU represents motion and orientation in a first reference frame defined by the IMU, the code further comprises code to cause the processor to:

translate the multi-axis motion data from the first reference frame to a second reference fixed with respect to gravity to yield translated multi-axis motion data;

decompose the translated multi-axis motion data into transverse motion components and vertical motion components in the second reference frame, the transverse motion components parallel to a ground plane; and calculate power expended by the animal body based on the transverse motion components, the vertical motion components, and the air-induced power.

23. The apparatus of claim 20, wherein the code further comprises code to cause the processor to:

calculate a metabolic energy expenditure of the animal based on the air-induced power.

24. The method of claim 1, wherein;

the sensor housing is coupled to a first foot of the animal body;

the pressure sensor is a first pressure sensor; and the plurality of pressure measured pressures is a first plurality of measured pressures, the method further comprising:

measuring, using a second pressure sensor coupled to a second foot of the animal body, a second plurality of measured pressures; and calculating a velocity of a cross wind based on the first plurality of measured pressures and the second plurality of measured pressures.

25. The apparatus of claim 20, wherein the code to cause the processor to receive signals indicating the plurality of pressures further includes code to cause the processor to receive signals indicating the plurality of pressures while the pressure sensor is coupled to an anterior portion of the foot.

26. A method, comprising:

measuring, a plurality of positions and orientations of an animal body in motion using a first sensor coupled to an anterior portion of an animal body, the first sensor including an inertial measurement unit (IMU) and a first pressure sensor disposed within a pressure chamber defined by a housing of the first sensor, an opening in the housing placing the pressure chamber in fluid communication with an exterior of the housing;

measuring, using the first pressure sensor, a plurality of anterior measured pressures;

measuring, using a second pressure sensor from a second sensor coupled to a posterior portion of the animal body, a plurality of posterior measured pressures;

correlating, each position and orientation from the plurality of positions and orientations to at least one of the plurality of anterior measured pressures or the plurality of posterior measured pressures to;

calculating, by a processor, a static pressure based on the correlated positions and orientations and at least one of the plurality of anterior measured pressures or the plurality of posterior measured pressures;

calculating, by the processor, a maximum pressure of at least one of the plurality of anterior measured pressures or the plurality of posterior measured pressures; and calculating an air-induced power exerted on an entirety of the animal body based on the static pressure and the maximum pressure.

27. The method of claim 26, further comprising calculating a velocity of a head wind or a tail wind based on a difference between the plurality of anterior measured pressures and the plurality of posterior measured pressures, the air-induced power calculated based on the velocity of the head wind or the tail wind.

* * * * *